(12) United States Patent
Grissett et al.

(10) Patent No.: US 7,381,692 B2
(45) Date of Patent: *Jun. 3, 2008

(54) BAR SOAP WITH FIBROUS ASSEMBLY

(75) Inventors: Gregory Aaron Grissett, Jacksonville, NC (US); Filomena Augusta Macedo, Naugatuck, CT (US); Diane Marie Keenan, Derby, CT (US); David Robert Williams, Monroe, CT (US)

(73) Assignee: Unilever Home & Personal Care, USA Division of Conopco, Inc., Greenwich, CT (US)

( * ) Notice: Subject to any disclaimer, the term of this patent is extended or adjusted under 35 U.S.C. 154(b) by 239 days.

This patent is subject to a terminal disclaimer.

(21) Appl. No.: 11/008,528

(22) Filed: Dec. 9, 2004

(65) Prior Publication Data

US 2005/0276828 A1    Dec. 15, 2005

Related U.S. Application Data

(60) Provisional application No. 60/579,592, filed on Jun. 14, 2004.

(51) Int. Cl.
*C11D 17/04*    (2006.01)
*C11D 11/00*    (2006.01)

(52) U.S. Cl. ........... 510/141; 510/142; 510/156; 510/439

(58) Field of Classification Search .......... None
See application file for complete search history.

(56) References Cited

U.S. PATENT DOCUMENTS

| | | |
|---|---|---|
| 3,668,054 A | 6/1972 | Stumpf |
| 4,190,550 A | 2/1980 | Campbell |
| 4,969,225 A | 11/1990 | Schubert |
| 5,221,506 A | 6/1993 | Dulin |
| 6,171,007 B1 | 1/2001 | Hsu |
| 6,190,079 B1 | 2/2001 | Ruff |
| 6,428,799 B1 | 8/2002 | Cen et al. |
| 6,491,933 B2 | 12/2002 | Lorenzi et al. |
| 6,491,937 B1 * | 12/2002 | Slavtcheff et al. .......... 424/402 |
| 6,503,520 B1 | 1/2003 | Afriat |
| 6,607,734 B1 | 8/2003 | Afriat |
| 6,689,345 B2 | 2/2004 | Jager Lezer |
| 6,783,294 B2 | 8/2004 | Duden et al. |

(Continued)

FOREIGN PATENT DOCUMENTS

| | | |
|---|---|---|
| EP | 1090627 | 11/2001 |
| FR | 2 271 808 | 12/1975 |
| GB | 1473147 | 5/1977 |
| WO | 01/08658 | 2/2001 |
| WO | 2005/007789 | 1/2005 |

OTHER PUBLICATIONS

International Search Report, PCT/EP2005/006074, mailed Oct. 24, 2005, 3 pp.

*Primary Examiner*—Necholus Ogden
(74) *Attorney, Agent, or Firm*—Alan A. Bornstein

(57) ABSTRACT

A cleansing article composed of a solid or semi-solid foamable composition and a batting layer with bonded fibers is described that provides the user with a pleasant personal cleansing experience and which in one embodiment combines cleansing, aesthetic and/or skin benefit with active agents and exfoliation. The user also experiences substantial lather during use of the cleansing article. The batting layer is at least partially encompassed by the solid or semi-solid foamable composition.

12 Claims, 5 Drawing Sheets

U.S. PATENT DOCUMENTS

| | | |
|---|---|---|
| 6,896,435 B1 | 5/2005 | Rink |
| 2001/0018068 A1 | 8/2001 | Lorenzi et al. |
| 2003/0064901 A1* | 4/2003 | Diez ......................... 510/141 |
| 2003/0100236 A1 | 5/2003 | Seth et al. |
| 2003/0220212 A1 | 11/2003 | Devitis |
| 2004/0033915 A1 | 2/2004 | Aleles et al. |
| 2004/0176002 A1* | 9/2004 | Siegwart ..................... 442/35 |
| 2005/0113270 A1 | 5/2005 | Stockman et al. |

\* cited by examiner

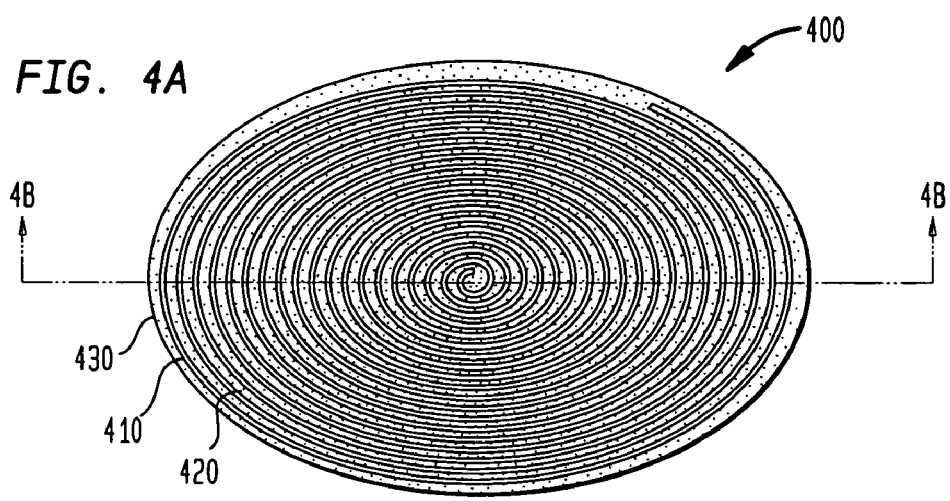
FIG. 4A
FIG. 4A1
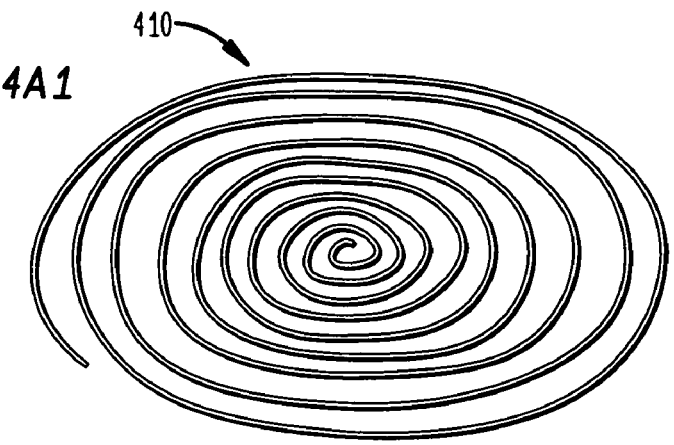
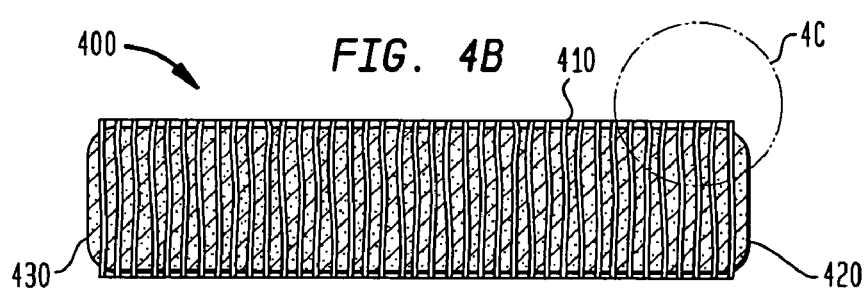
FIG. 4B
FIG. 4C
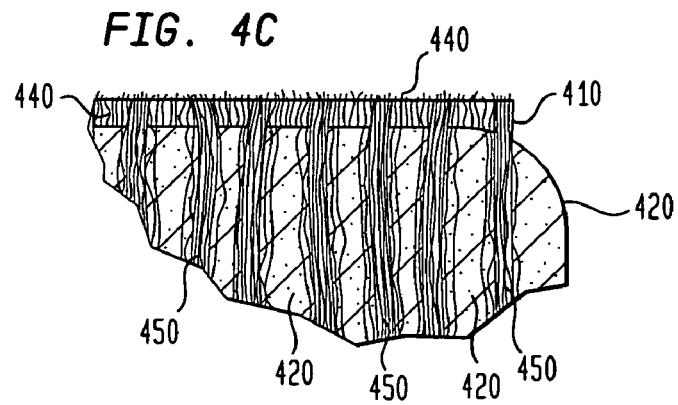

BAR SOAP WITH FIBROUS ASSEMBLY

This application claims priority from U.S. Provisional Application No. 60/579,592 filed on Jun. 14, 2004.

BACKGROUND OF THE INVENTION

1. Field of the Invention

The invention relates to a personal cleansing article and more specifically to a personal cleansing article wherein a toilet bar composed of skin cleansing and optional aesthetic, skin benefit and/or skin active compositions contains a fibrous structure disposed at least partially throughout the bar.

2. The Related Art

Toilet bar skin cleaning properties are well known. An ideal bar composition not only cleans but provides a large quantity of lather and leaves the skin feeling comfortable. Consumers also desire to obtain toilet bars with good hardness, low mush, and that optionally contain appealing aesthetic ingredients such as fragrances, one or more skin conditioning agents such as emollients for moisturizing the skin and one or more skin active agents for treating the skin according to individual preferences and needs. To accomplish this, a wide variety of fibrous structures have been suggested for inclusion in toilet bars.

GB patent no. 1,473,147 issued to Minnesota Mining and Manufacturing Company on May 11, 1977 describes pads of nonwoven fibers containing a solid core of surfactant material for cleaning the human body. Fibers used may be at least 3 cm length and 20 to 200 microns in diameter. Two manufacturing processes are described. The first entangles a loose assembly of crimped fibers around a shaped solid core of soap via felting needles. The second process pre-needles an assembly of loose fibers into a seamless ball and subsequently requires injecting a molten soap into the interior of the ball. U.S. Pat. No. 4,190,550 issued to Campbell on Feb. 26, 1980 discloses a similar article and manufacturing method as described in GB 1,473,147, Both of the above mentioned prior art examples are not economically feasible nor do the examples provide the benefits of lather generation and exfoliation.

U.S. Pat. No. 4,969,225 issued to Schubert on Nov. 13, 1990 describes a bathing and cleansing article comprising an internal cavity into which the bar soap can be inserted. The article is constructed of elastic, resilient synthetic fibrous batt or open-cell chemical foam. This structure is disadvantageous since by enclosing bar soaps with the batt or foam structure, excess water is retained within the bar soap structure causing premature dissolution and softening of the soap.

U.S. Pat. No. 5,2221,506 issued to Dulin on Jun. 22, 1993 describes a bar soap for personal use having a structural center selected from an open celled sponge material, or woven or nonwoven organic filamentary material. Specifically the core comprises 5-%- to 50-% of the volume of soap bar.

U.S. Pat. No. 6,190,079 issued to Ruff on Feb. 20, 2001 describes a scrubbing soap bar that includes an imbedded scrubber in a defined portion of the bar and which is partially exposed such that fingers can be inserted for improved handability of the soap bar.

U.S. Publication No. 2003/0220212 to DeVitis and published on Nov. 27, 2003 describes a reinforced bar soap with the purpose to prolong the usage of conventional bar soap and reduce consumption. This invention contemplates a reinforcement member in an interior portion thereof. The reinforcement member is preferably at a core position in the interior portion. Reinforced bar soaps are provided, for example, which comprise at least one mesh-type reinforcement member.

U.S. Publication No. 2004/0033915 to Aleles et al. and published on Feb. 19, 2004 describes a cleansing bar having improved latherability containing discrete elements having a length to diameter ratio of from about 50 to 1 to about 100,000 to 1; i.e. a non-continuous network of fibers without fiber to fiber bonds. There is no disclosure of a continuous network of fibers used in the cleansing bar.

U.S. Publication No. 2002/0025215, to Duden et al and published on Feb. 28, 2002 discloses a cleansing article marketed as J & J Body Scrub® which comprise a solid cleanser holder comprising at least one textured film having texture variations including at least one aperture and a solid cleanser, wherein the textured film surrounds the solid cleanser.

Surprisingly it has been found that a personal cleansing article composed of a toilet bar having specific percent energy loss, porosity, and/or yield stress property(ies) combined with a batting layer at least partially encompassed by the bar can be prepared. Such an article has improved lather generation, good aesthetics and beneficial in-use sensory results to the user.

SUMMARY OF THE INVENTION

In one aspect of the invention is a cleansing article, including but not limited to the following:
  a. a fibrous layer composed of a continuous network of bonded fibers where substantially all of the fiber bonds are manmade, said layer having a porosity of greater than about 0.95 and a percent energy loss of less than about 30;
  b. a solid or semi-solid foamable composition, preferably with a yield stress in the range of about 50 kPa to about 400 kPa at 25 C; said layer at least partially encompassed by said composition (defined as said layer and said composition being inseparable during cleansing until at least 50% of the foamable composition has been used up), the foamable composition to the layer being in the weight ratio range of about 30 to 1 to about 2000 to 1.

In another aspect of the invention is a cleansing article, including but limited to the following:
  a. a fibrous layer composed of a continuous network of bonded fibers, said layer having a porosity of greater than about 0.95 and a percent energy loss of less than about 30;
  b. a solid or semi-solid foamable composition, said layer at least partially encompassed by said composition, the foamable composition to the layer being in the weight ratio range of about 30 to 1 to about 2000 to 1, and
  c. wherein the layer prior to impregnation with the foamable composition is characterized by either a
    1. a non-woven or woven fibrous network selected from a corrugated bulky fabric having attached pleats oriented substantially perpendicularly to the x-y plane of the cleansing article,
    2. a bulky fabric having a plurality of discrete peaks forming a 3 dimensional pattern where the z axis of the fabric is oriented substantially perpendicularly to the x-y plane of the cleansing article,
    3. a bulky fabric having a polygonal regular or irregular 3 dimensional honeycomb-like structure where the z axis of the honeycomb-like fabric is oriented substantially perpendicularly to the x-y plane of the cleansing article, or
4. a bulky fabric having a plurality of attached layers oriented substantially perpendicularly to the x-y plane of the cleansing article and where the attached layers are arranged in a pattern composed of one or more of spiral, wavy or folded arrangement(s).

Preferred embodiments of the invention will now be described by way of example with reference to the accompanying drawings wherein like figures represent like features.

BRIEF DESCRIPTION OF THE DRAWINGS

FIG. 4A is a top planar view showing a fourth embodiment of the cleansing article of the present invention.

FIG. 4A1 is a top planar view of the bulky fabric component of the embodiment shown in FIG. 4A in a loose state.

FIG. 4B is a cross section taken along line 3-3 of FIG. 4A.

FIG. 4C is an enlarged partial view of the embodiment of the cleansing article shown in FIG. 4B.

DETAILED DESCRIPTION OF THE INVENTION

Figure 1A:
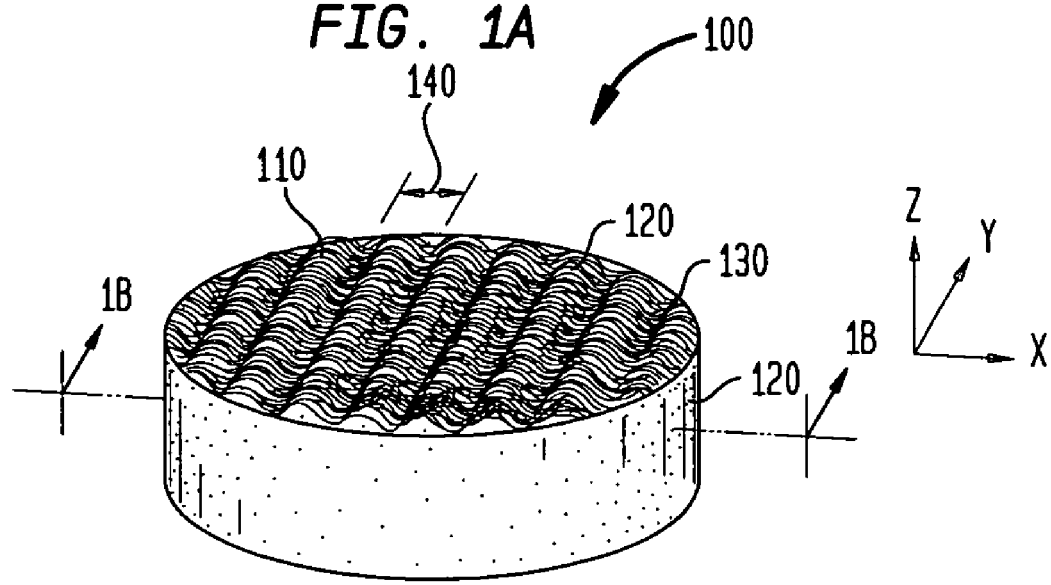
FIG. 1A is a perspective view showing one embodiment of the cleansing article of the present invention.

In one aspect of the invention is a cleansing article, including but not limited to the following:
a. a fibrous layer composed of a continuous network of bonded fibers where substantially all of the fiber bonds are manmade and preferably having about 1 to about 5 fiber to fiber bonds selected from one or a combination of chemical or thermal bonds per cubic millimeter, said layer having a porosity of greater than about 0.95 and a percent energy loss of less than about 30;
b. a solid or semi-solid foamable composition, preferably with a yield stress of the composition and fibrous layer composite in the range of about 50 kPa to about 400 kPa at 25 C; more preferably in the range of about 100 kPa to 350 kPa, and most preferably in the range of about 150 kPa to 250 kPa or optionally 350 kPa; said layer at least partially encompassed by said composition, the foamable composition to the layer being in the weight ratio range of about 30 to 1 to about 2000 to 1; preferably about 100 to 1 to about 1200 to 1, and more preferably about 100 to 1 to about 900 to 1.

Advantageously the cleansing article has a lather improvement factor greater than about 1.25, preferably greater than about 1.5, 1.75 or 2.0 using the test method described below. In a preferred embodiment the inventive cleansing article has a standard lather volume greater than about 150 ml, preferably greater than about 175 ml, 200 ml or 225 ml.

Preferably the fibrous layer of the inventive cleansing article prior to impregnation with the foamable composition is characterized by a density of about 0.0041 g/cubic cm. to about 0.1 g/cubic cm. More preferably this layer prior to impregnation with the foamable composition is characterized by air permeability in the range of about 200 to 900 cubic ft/sq. ft./min.

In a preferred embodiment the inventive cleansing article includes an aesthetic ingredient, a skin conditioning ingredient, a skin active ingredient or a blend thereof. Preferably the aesthetic ingredient is selected from fragrances, colorants, pigments, cosmetics, suspended bodies or blends thereof; the skin conditioning ingredient is selected from hydrophobic emollients and hydrophilic emollients or blends thereof, and the skin active material is selected from anti-wrinkle ingredients, skin lightening ingredients, vitamins, antimicrobial ingredients, acne medications, exfoliating agents, astringent ingredients, antioxidant ingredients, enzymes, sunscreen ingredients or blends thereof. More preferably the skin conditioning ingredient includes a hydrophobic emollient selected from silicone oil(s), gum(s); fat(s), di or triglyceride oil(s), wax(es); hydrophobic plant extract(s), fatty acid(s), fatty ester(s), hydrocarbon(s) or blends thereof.

Advantageously the foamable composition of the inventive cleansing article includes an amphoteric surfactant. Preferably the foamable composition further includes a component in a concentration of about 15 to 80% by wt. selected from C8 to C24 acyl isethionate(s), soap(s), or blends thereof.

In a preferred embodiment, the inventive cleansing article contains a layer that prior to its impregnation with the foamable composition is characterized by fibers selected from polyethylene terephthalate, polyethylene, polypropylene, nylon, rayon or cotton fibers or blends thereof. Advantageously this layer prior to impregnation with the foamable composition is characterized by a basis weight in the range of about 1 oz/sq. yd to about 20 oz/sq. yd.

In another aspect of the invention is a cleansing article, including but limited to the following:
a. a fibrous layer composed of a continuous network of bonded fibers, said layer having a porosity of greater than about 0.95 and a percent energy loss of less than about 30;
b. a solid or semi-solid foamable composition, said layer at least partially encompassed by said composition, the foamable composition to the layer being in the weight ratio range of about 30 to 1 to about 2000 to 1, and
c. wherein the layer prior to impregnation with the foamable composition is characterized by either a
1. a non-woven or woven fibrous network selected from a corrugated bulky fabric having attached pleats oriented substantially perpendicularly to the x-y plane of the cleansing article (preferably having about 1 to 6 pleats per inch),
2. a bulky fabric having a plurality of discrete peaks forming a 3 dimensional pattern where the z axis of the fabric is oriented substantially perpendicularly to the x-y plane of the cleansing article (preferably where the peaks are in the range of 0.25 to 3 per square cm),
3. a bulky fabric having a polygonal regular or irregular 3 dimensional honeycomb-like structure where the z axis of the honeycomb-like fabric is oriented substantially perpendicularly to the x-y plane of the cleansing article, or 4. a bulky fabric having a plurality of attached layers oriented substantially perpendicularly to the x-y plane of the cleansing article and where the attached layers are arranged in a pattern composed of one or more of spiral, wavy or folded arrangement(s).

Figure 1B:
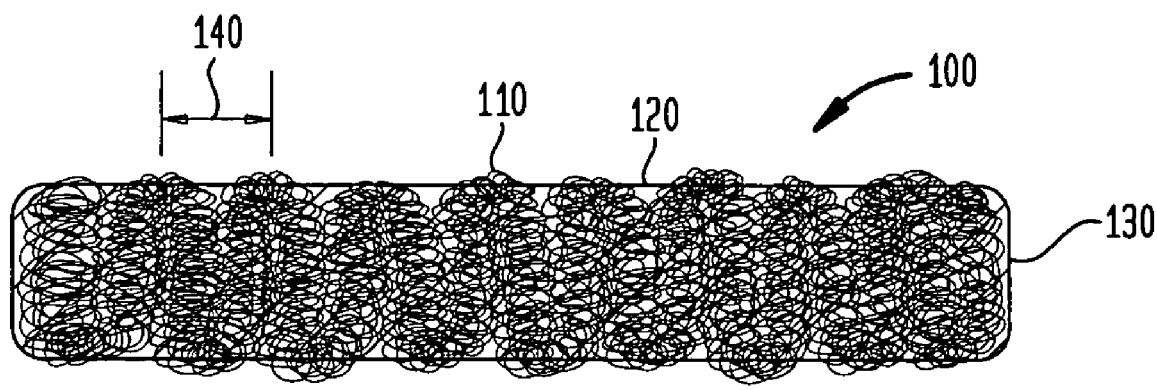
FIG. 1B is a cross section taken along line 1B of FIG. 1A.

Referring to FIG. 1A, cleansing article 100 is composed of a fibrous layer made up of a continuous network of bonded fibers 110 in the form of a corrugated bulky fabric having attached pleats 140 oriented substantially perpendicularly to the x-y plane of article 100. A solid or semi-solid foamable composition 120 is distributed substantially uniformly within the interior of article 100 and around fibers 110. Some of the fibers 110 are exposed to the air at the outer surface 130 of article 100. Outer surface is here defined as the air-article interface of the cleansing article. FIG. 1B shows a cross section taken along line 1B of FIG. 1.

Figure 2A:
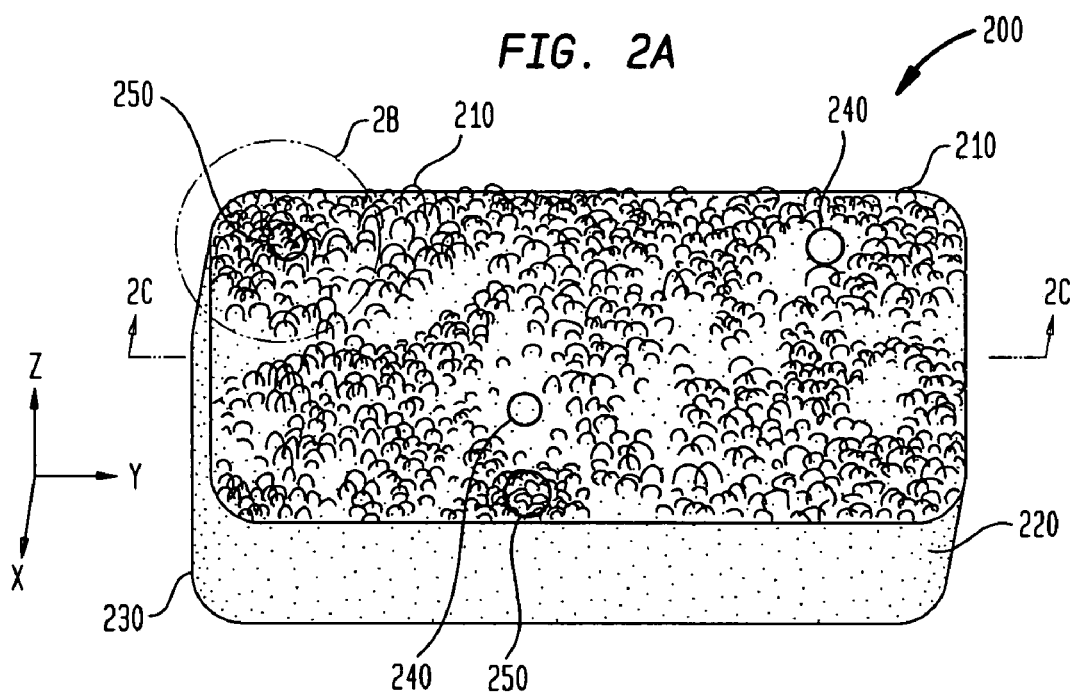
FIG. 2A is a perspective view showing a second embodiment of the cleansing article of the present invention.
Figure 2B:
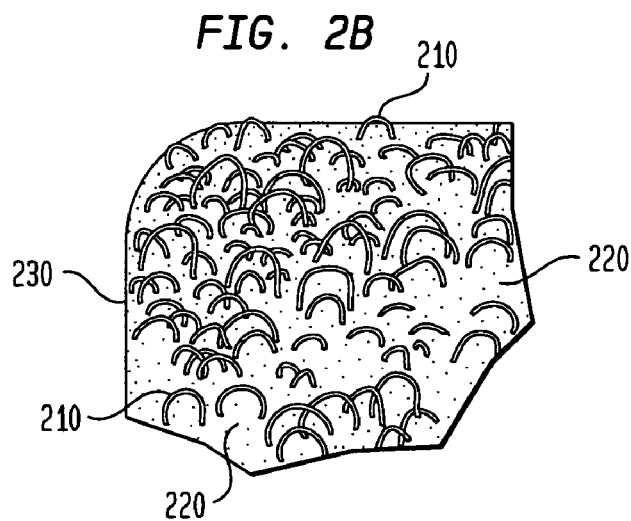
FIG. 2B is an enlarged partial view of the embodiment of the cleansing article shown in FIG. 2A.
Figure 2C:
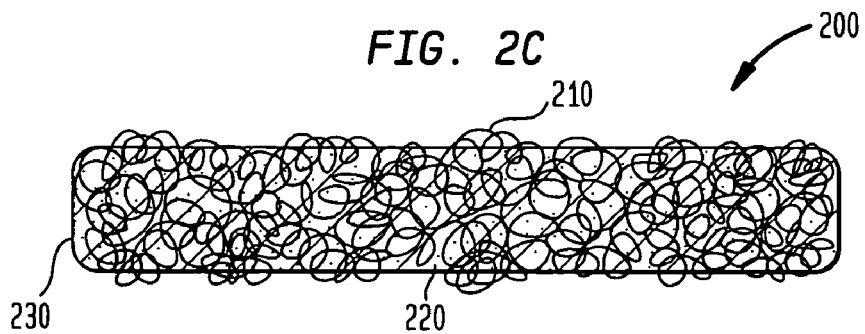
FIG. 2C is a cross section taken along line 2C of FIG. 2A.

Now referring to FIG. 2A, cleansing article 200 is composed of a fibrous layer having a continuous network of bonded fibers 210 in the form of a bulky fabric having a plurality of discrete valleys 240 and peaks 250 forming a 3 dimensional pattern where the z axis of the fabric is oriented substantially perpendicularly to the x-y plane of article 200. A solid or semi-solid foamable composition 220 is distributed substantially uniformly within the interior of article 200 and around fibers 210. Some of the fibers 210 are exposed to the air at the outer surface 230 of article 200. FIG. 2B shows a partial detailed view of the outer surface of article 200 shown in FIG. 2A. FIG. 2C shows a cross section taken along line 2C of FIG. 2A.

Figure 3A:
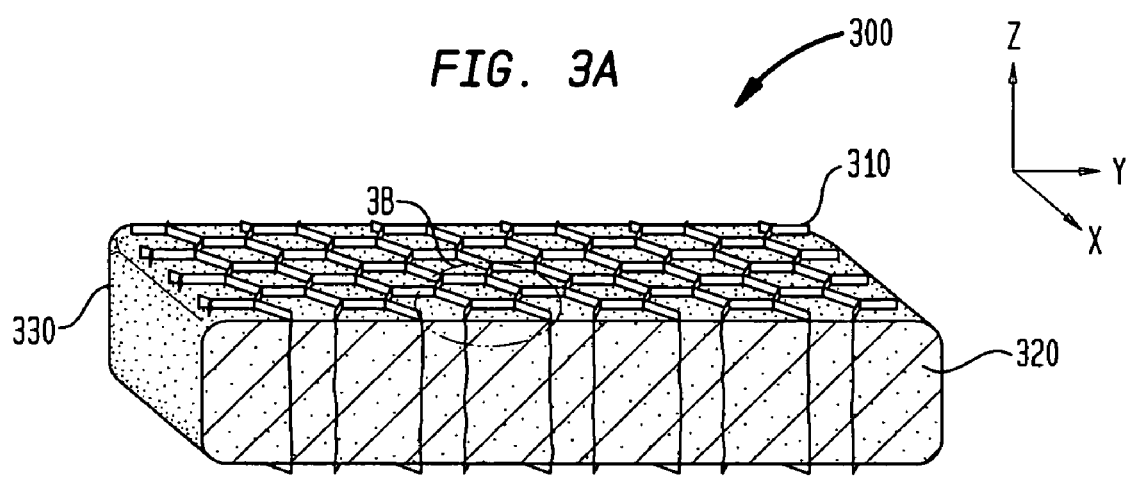
FIG. 3A is a perspective view showing a third embodiment of the cleansing article of the present invention.
Figure 3B:
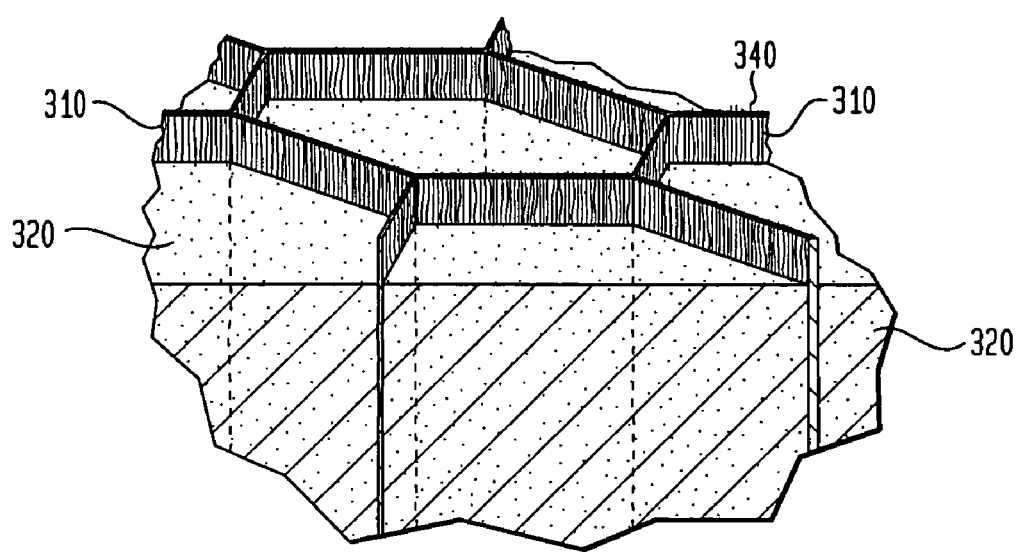
FIG. 3B is an enlarged partial view of the embodiment of the cleansing article shown in FIG. 3A.

Now referring to FIG. 3A, cleansing article 300 is composed of a bulky fabric 310 having a continuous network of bonded fibers 340 with a polygonal regular 3 dimensional honeycomb-like structure where the z axis of the honeycomb-like fabric. 310 is oriented substantially perpendicularly to the x-y plane of article 300. A solid or semi-solid foamable composition 320 is distributed substantially uniformly within the interior of article 200 and around the bulky fabric 310. Some of the fibers 340 are exposed to the air at the outer surface 330 of article 300. FIG. 3B is an enlarged partial perspective view of the outer surface 330 of article 300 shown in FIG. 3A.

Now referring to FIG. 4A, cleansing article 400 is composed of a bulky fabric 410 having a continuous network of bonded fibers 440 where fabric 410 is arranged in a spiral pattern and oriented substantially perpendicularly to the x-y plane of article 400. A solid or semi-solid foamable composition 420 is distributed substantially uniformly within the interior of article 400 and around fabric 410. Some of the fibers 440 are exposed to the air at the outer surface 430 of article 400. FIG. 4A1 shows fabric 410 depicted in FIG. 4A in a loosely coiled state before being fabricated into article 400. FIG. 4B shows a cross section taken along line 4B of FIG. 4A. FIG. 4C is an enlarged partial perspective view of the outer surface 430 of article 400 shown in FIG. 4B. In a preferred embodiment, fabric 410 is coiled into a loose or tight spiral or folded arrangement and adjacent layers may optionally be attached in a random or regular pattern or combination thereof by any art recognized or equivalent technique(s) such as heat or ultrasonic bonding, needle punching or other fiber entangling process, stitching, stapling or use of other fasteners, adhesive bonding, any combination thereof and the like. Such attachment(s) would desirably be effective to prevent substantial uncoiling or unfolding of fabric 410 during manufacture or use of the cleansing article.

Surfactants:

Surfactants are an essential component of the inventive toilet bar. They are compounds that have hydrophobic and hydrophilic portions that act to reduce the surface tension of the aqueous solutions they are dissolved in. Useful surfactants can include soap(s), and non-soap anionic, nonionic, amphoteric, and cationic surfactants, and blends thereof.

Anionic Surfactants:

Fatty Acid Soap

In the subject invention, soluble soaps may optionally comprise 2-25%, preferably 2-10% by wt. of the foamable composition of the inventive article. Soluble soap is defined as a soap or soap blend having a Krafft point less than or equal to about 40 C. The soluble soap(s) can be selected from the chain length of C6-C14 saturated fatty acid soap(s) and C16-C18 unsaturated and polyunsaturated fatty acid soap(s) or a combination of these fatty acid soaps. Here the Krafft point of the soap is defined as the temperature at which the solubility of the soap rises sharply. These soluble soaps can be derived from coco fatty acid, Babasu fatty acid, palm kernel fatty acid and any other source of unsaturated fatty acid including tallow and vegetable oils and their mixtures. The soap may be prepared from coconut oils in which case the fatty acid content of C12-C18 is about 85%. In addition to specific "soluble" soap, additional soap(s), which may not be as soluble, may be used. These soap components are here referred as insoluble soaps. The insoluble soap components can be in the range of 5-20% as structurant for the foamable composition of the inventive article.

The term "soap" is used here in its popular sense, i.e., the alkali metal or alkanol ammonium salts of aliphatic alkane- or alkene monocarboxylic acids. Sodium, potassium, mono-, di- and tri-ethanol ammonium cations, or combinations thereof, are suitable for purposes of this invention. In general, sodium soaps are used in the compositions of this invention, but from about 1% to about 25% of the soap may be potassium soaps. Overall the soap(s) useful herein are the well known alkali metal salts of natural of synthetic aliphatic (alkanoic or alkenoic) acids having about 12 to 22 carbon atoms, preferably about 12 to about 18 carbon atoms. They may be described as alkali metal carboxylates of hydrocarbons having about 12 to about 22 carbon atoms. The soaps may contain unsaturation in accordance with commercially acceptable standards. Excessive unsaturation is normally avoided to minimize the color and odor issues.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric (C 12), myristic (C 14), palmitic (C 16), or stearic (C 18) acids with an alkali metal hydroxide or carbonate.

Synthetic Anionic Surfactants

The foamable composition of the present invention optionally contains one or more non-soap anionic detergents (syndets). Preferably the syndets have a zein value of 50 or less. Zein value may be measured using the test method described below. Advantageously non-soap anionic detergents or surfactants are used from about 3, 9 or 15% by wt. to about 9, 15 or 21% by wt.

The anionic detergent active which may be used may be aliphatic sulfonates, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or aromatic sulfonates such as alkyl benzene sulfonate.

The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1, preferably greater than 3; and M is a solubilizing cation such as sodium, potassium, ammonium or substituted ammonium. Ammonium and sodium lauryl sulfates, lauryl ether sulfates and their mixtures are preferred.

The anionic may also be alkyl sulfosuccinates (including mono- and dialkyl, e.g., $C_6$-$C_{22}$ sulfosuccinates); alkyl and acyl taurates, alkyl and acyl sarcosinates, sulfoacetates, $C_8$-$C_{22}$ alkyl phosphates, alkyl phosphate esters and alkoxyl alkyl phosphate esters, acyl lactates, $C_8$-$C_{22}$ monoalkyl succinates and maleates, sulphoacetates, alkyl glucosides and acyl isethionates, and the like.

Sulfosuccinates may be monoalkyl sulfosuccinates having the formula:

$$R^4O_2CCH_2CH(SO_3M)CO_2M; \text{ and}$$

amide-MEA sulfosuccinates of the formula;

$$R^4CONHCH_2CH_2O_2CCH_2CH(SO_3M)CO_2M$$

wherein $R^4$ ranges from $C_8$-$C_{22}$ alkyl and M is a solubilizing cation.

Sodium and ammonium alkylethoxy (1-5 eo) sulfosuccinates, especially lauryl ethoxy (3 eo) sulfosuccinate are especially useful.

Sarcosinates are generally indicated by the formula:

$$R^1CON(CH_3)CH_2CO_2M,$$

wherein $R^1$ ranges from $C_8$-$C_{20}$ alkyl and M is a solubilizing cation.

Taurates are generally identified by formula:

$$R^2CON(R^3)CH_2CH_2SO_3M$$

wherein $R^2$ ranges from $C_8$-$C_{20}$ alkyl, $R^3$ may be H or $C_1$-$C_4$ alkyl and M is a solubilizing cation.

The inventive skin care or foamable composition may contain $C_8$-$C_{14}$ acyl isethionates. These esters are prepared by reaction between alkali metal isethionate with mixed aliphatic fatty acids having from 6 to 12 carbon atoms and an iodine value of less than 20.

The acyl isethionate may be an alkoxylated isethionate such as is described in Ilardi et al., U.S. Pat. No. 5,393,466, titled "Fatty Acid Esters of Polyalkoxylated isethonic acid; issued Feb. 28, 1995; hereby incorporated by reference. This compound has the general formula:

$$RC-O(O)-CH(X)-CH_2-(OC(Y)H-CH_2)_m-SO_3M^+$$

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

In some applications, it is desirable that the foamable composition be in the form of an aqueous gel as described in more detail below. For such a composition, it has been found advantageous that all or part of the cations of the anionic surfactants are nitrogenous. Preferably such cations include ammonium or alkanolammonium cations or a blend thereof.

Amphoteric Surfactants

One or more amphoteric surfactants may be used in this invention. Advantageously amphoteric surfactants are used from about 3, 9 or 15% by wt. to about 9, 15 or 21% by wt. Such surfactants include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

$$R^1-[-C(O)-NH(CH_2)_n-]_m-N^+-(R^2)(R^3)X-Y$$

where $R^1$ is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and Y is $-CO_2-$ or $-SO_3-$ Suitable amphoteric surfactants within the above general formula include simple betaines of formula:

$$R^1-N^+-(R^2)(R^3)CH_2CO_2^-$$

and amido betaines of formula:

$$R^1-CONH(CH_2)_n-N^+-(R^2)(R^3)CH_2CO_2^-$$

where n is 2 or 3.

In both formulae $R^1$, $R^2$ and $R^3$ are as defined previously. $R^1$ may in particular be a mixture of $C_{12}$ and $C_{14}$ alkyl groups derived from coconut oil so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

$$R^1-N^+-(R^2)(R^3)(CH_2)_3SO_3^-$$

or $$R^1-CONH(CH_2)_m-N^+-(R^2)(R^3)(CH_2)_3SO_3^-$$

where m is 2 or 3, or variants of these in which $-(CH_2)_3SO_3^-$ is replaced by $$-CH_2C(OH)(H)CH_2SO_3^-$$

In these formulae $R^1$, $R^2$ and $R^3$ are as discussed previously.

A preferred sulfobetaine is cocoamidopropyl hydroxy sultaine

Amphoacetates and diamphoacetates are also intended to be covered in the zwitterionic and/or amphoteric compounds which are used such as e.g., sodium lauroamphoacetate, sodium cocoamphoacetate, and blends thereof, and the like.

Nonionic Surfactants

One or more nonionic surfactants may also be used in foamable composition of the inventive article composition of the present invention. When present, nonionic surfactants may be used at levels as low as about about 3, 6 or 9% by wt. to about 9, 18 or 27% by wt.

The nonionics which may be used include in particularly the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$-$C_{22}$) phenols ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

The nonionic may also be a sugar amide, such as a polysaccharide amide. Specifically, the surfactant may be one of the lactobionamides described in U.S. Pat. No. 5,389,279 to Au et al. titled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

Cationic Skin Conditioning Agents

An optional component in the foamable composition according to the invention is a cationic skin feel agent or polymer, such as for example cationic celluloses. Advantageously cationic skin feel agent(s) or polymer(s) are used from about 0.2, 5 or 10% by wt. to about 5, 10 or 15% by wt. Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200, and quaternary ammonium compounds such as alkyldimethylammonium halogenides.

A particularly suitable type of cationic polysaccharide polymer that can be used is a cationic guar gum derivative, such as guar hydroxypropyltrimonium chloride (Commercially available from Rhone-Poulenc in their JAGUAR trademark series). Examples are JAGUAR C13S, which has a low degree of substitution of the cationic groups and high viscosity, JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Particularly preferred cationic polymers are JAGUAR C13S, JAGUAR C15, JAGUAR C17 and JAGUAR C16 and JAGUAR C162, especially Jaguar C13S. Other cationic skin feel agents known in the art or their equivalents may be used provided that they are compatible with the inventive formulation.

Other preferred cationic compounds that are useful in the present invention include amido quaternary ammonium compounds such as quaternary ammonium propionate and lactate salts, and quaternary ammonium hydrolyzates of silk or wheat protein, and the like. Many of these compounds can be obtained as the Mackine™ Amido Functional Amines, Mackalene™ Amido functional Tertiary Amine Salts, and Mackpro® cationic protein hydrolysates from the McIntyre Group Ltd. (University Park, Ill.).

In a preferred embodiment of the invention having a hydrolyzed protein conditioning agent, the average molecular weight of the hydrolyzed protein is preferably about 2500. Preferably 90% of the hydrolyzed protein is between a molecular weight of about 1500 to about 3500. In a preferred embodiment, MACKPRO™ WWP (i.e. wheat germ amido dimethylamine hydrolyzed wheat protein) is added at a concentration of 0.1% (as is) in the foamable composition of the inventive article. This results in a MACKPRO™ WWP "solids" of 0.035% in the final foamable composition of the inventive article formula for this embodiment.

Cationic Surfactants

One or more cationic surfactants may also be used in the inventive foamable composition of the inventive article article composition. Advantageously cationic surfactants are used from about 3, 5 or 7% by wt. to about 7, 12 or 17% by wt.

Examples of cationic detergents are the quaternary ammonium compounds such as alkyldimethylammonium halogenides.

Other suitable surfactants which may be used are described in U.S. Pat. No. 3,723,325 to Parran Jr. titled "Detergent Compositions Containing Particle Deposition Enhancing Agents" issued Mar. 27, 1973; and "Surface Active Agents and Detergents" (Vol. I & II) by Schwartz, Perry & Berch, both of which are also incorporated into the subject application by reference.

Gelling Agents

It is desirable to include a gelling agent when the foamable composition is a gel, especially an aqueous gel. One type or class of preferred gelling agent is a thermo-reversible gelling agent or agents. By the term "thermo-reversible gelling agent" we mean materials that form a gel having a definite melting temperature range above which the composition is fluid (the "sol") and below which the composition is a gel having a yield stress. Although such materials are well known in the art, not all are compatible and form gels with surfactant containing liquids.

Preferred thermo-reversible gelling agents include biopolymers, certain hydrophobically modified synthetic polymers, liquid crystal forming surfactants that exhibit a distinct melting temperature. Examples of such materials include proteins like gelatin; polysaccharides like carrageenan, especially kappa carrageenan, gellan, locust bean gum, agar and alginate; hydrophobically modified hydroxyethyl cellulose and starch, hydrophobically modified urethanes; mixtures of straight chain anionic and amphoteric surfactants with low HLB amphiphiles of appropriate chain length; and mixtures thereof.

Another class of gelling agents are those that form gels in response to various composition stimuli such as pH or type of electrolyte employed. These include synthetic polymers such as crosslinked acrylic polymers containing acrylic or methacrylic acid monomers, e.g., carbomers and polyvinyl alcohol and its partial esters, e.g., vinylalcohol/vinyl acetate copolymers. The former polymers are gel in response to pH while the latter can be gelled by the addition of an appropriate electrolyte such as borax. An especially preferred thermo-reversible gelling polymer is gelatin having a bloom strength greater than 100 and preferably greater than 200.

The gelling agent is present at a level in the foaming composition sufficient to provide a yield stress between about 50 and about 450 kPa at 25 C The yield stress can be measured via a wire cutter type measurement (e.g., "cheese cutter") or it can be expressed as a penetrometer based value as is well known in the food industry measurement, e.g., the Bloom method. Generally, the polymer gelling agent is present at a level between about 0.1 to about 15% by weight of the foamable composition.

In addition to the thermo-reversible gelling polymer, additives can also be incorporated that modify either the melting point range of the gel or the gel strength. One class of gel modifying additive are electrolytes that provide mono and divalent cations such as sodium, potassium and calcium. Another class of additive is a non-gelling polymer such as guar, modified quar and linear synthetic water soluble polymers. A third class of gel modifying additive is a water insoluble oil phase thickener such the Uniclear® sold by Arizona Chemicals and Thixcin® sold by Rheox. Mixtures of different types of gel-modifying additives can also be usefully employed.

For foamable compositions that are elastic gel, the gel strength can be measured either by the cheese cutter method described below or be various indentation methods well know for food gels, e.g., The "Bloom Test" and the like.

In addition, the foamable composition of the inventive article of the invention may include 0 to 15% by wt. optional ingredients as follows:

perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer) and the like; all of which are useful in enhancing the appearance or cosmetic properties of the product.

The compositions may further comprise preservatives such as dimethyloldimethylhydantoin (Glydant XL 1000), parabens, sorbic acid etc., and the like.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) and the like may be used advantageously in amounts of about 0.01% or higher if appropriate.

Skin conditioning agents such as emollients are advantageously used in the present invention. Hydrophilic emollients including humectants such as polyhydric alcohols, e.g. glycerin, sorbitol and propylene glycol, and the like; polyols such as the polyethylene glycols listed below, and the like; polyglycerol esters such as polyglyceryl-10 decaoleate and the like; urea, hydrophilic plant extracts; their analogues, derivatives and blends thereof and the like may be used. Advantageously humectants are used from about 0.1, 1 or 3% by wt. to 0.5, 3 or 6% by wt. based on the foamable composition. Humectants also may help to retaqin moisture in the actual cleansing article.

| | |
|---|---|
| Polyox WSR-205 | PEG 14M, |
| Polyox WSR-N-60K | PEG 45M, or |
| Polyox WSR-N-750 | PEG 7M. |

Hydrophobic emollients may be used in a wide concentration range in the inventive foamable composition of the inventive article. Advantageously hydrophobic emollients are used from about 0.1, 1 or 3% by wt. to 0.5, 3, 6, 10, 20, 30, 40, 50, or 50% by wt. or more based on the foamable composition. The term "emollient" is defined as a substance which softens or improves the elasticity, appearance, and youthfulness of the skin (stratum corneum) by increasing its water content, and keeps it soft by retarding the decrease of its water content.

Useful hydrophobic emollients include the following:
(a) silicone oils and modifications thereof such as linear and cyclic polydimethylsiloxanes; amino, alkyl, alkylaryl, and aryl silicone oils;
(b) fats and oils including natural fats and oils such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;
(c) waxes such as carnauba, spermaceti, beeswax, lanolin, and derivatives thereof;
(d) hydrophobic plant extracts;
(e) hydrocarbons such as liquid paraffin, petrolatum, microcrystalline wax, ceresin, squalene, pristan and mineral oil;
(f) higher fatty acids such as lauric, myristic, palmitic, stearic, behenic, oleic, linoleic, linolenic, lanolic, isostearic, arachidonic and poly unsaturated fatty acids (PUFA);
(g) higher alcohols such as lauryl, cetyl, stearyl, oleyl, behenyl, cholesterol and 2-hexydecanol alcohol;
(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;
(i) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starFlower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils; and
(j) mixtures of any of the foregoing components, and the like.

Preferred hydrophilic emollient moisturizing agents are selected from fatty acids, di and triglyceride oils, mineral oils, petrolatum, and mixtures thereof; with fatty acids being most preferred.

Exfoliants

The inventive cleansing article may contain particles that are greater than 50 microns in average diameter that help remove dry skin to supplement the exfoliating properties of the fibrous mat. Not wishing to be bound by theory, it is believed that the degree of exfoliation depends on the size and morphology of the particles. Large and rough particles are usually very harsh and irritating. Very small particles may not serve as effective exfoliants. Such exfoliants used in the art include natural minerals such as silica, talc, calcite, pumice, tricalcium phosphate; seeds such as rice, apricot seeds, etc; crushed shells such as almond and walnut shells; oatmeal; polymers such as polyethylene and polypropylene beads, flower petals and leaves; microcrystalline wax beads; jojoba ester beads, and the like. These exfoliants come in a variety of particle sizes and morphology ranging from micron sized to a few mm. They also have a range of hardness. Some examples are given in table A below.

TABLE A

| Material | Hardness (Mohs) |
| --- | --- |
| Talc | 1 |
| Calcite | 3 |
| Pumice | 4-6 |
| Walnut Shells | 3-4 |
| Dolomite | 4 |
| Polyethylene | ~1 |

Optional Active Agents

Advantageously, active agents other than skin conditioning agents defined above may be added to the cleansing article. These active ingredients may be advantageously selected from bactericides, vitamins, anti-acne actives; anti-wrinkle, anti-skin atrophy and skin repair actives; skin barrier repair actives; non-steroidal cosmetic soothing actives; artificial tanning agents and accelerators; skin lightening actives; sunscreen actives; sebum stimulators; sebum inhibitors; anti-oxidants; protease inhibitors; skin tightening agents; anti-itch ingredients; hair growth inhibitors; 5-alpha reductase inhibitors; desquamating enzyme enhancers; anti-glycation agents; or mixtures thereof; and the like.

These active agents may be selected from water soluble active agents, oil soluble active agents, pharmaceutically-acceptable salts and mixtures thereof. The term "active agent" as used herein, means personal care actives which can be used to deliver a benefit to the skin and/or hair and which generally are not used to confer a skin conditioning benefit, such are delivered by emollients as defined above. The term "safe and effective amount" as used herein, means an amount of active agent high enough to modify the condition to be treated or to deliver the desired skin care benefit, but low enough to avoid serious side effects. The term "benefit," as used herein, means the therapeutic, prophylactic, and/or chronic benefits associated with treating a particular condition with one or more of the active agents described herein. What is a safe and effective amount of the active agent ingredient will vary with the specific active agent, the ability of the active to penetrate through the skin, the age, health condition, and skin condition of the user, and other like factors. Preferably the compositions of the present invention comprise from about 0.0001% to about 50%, more preferably from about 0.05% to about 25%, even more preferably 0.1% to about 10%, and most preferably 0.1% % to about 5%, by weight of the active agent component.

Anti-acne actives can be effective in treating acne vulgaris, a chronic disorder of the pilosebaceous follicles. Nonlimiting examples of useful anti-acne actives include the keratolytics such as salicylic acid (o-hydroxybenzoic acid), derivatives of salicylic acid such as 5-octanoyl salicylic acid and 4 methoxysalicylic acid, and resorcinol; retinoids such as retinoic acid and its derivatives (e.g., cis and trans); sulfur-containing D and L amino acids and their derivatives and salts, particularly their N-acetyl derivatives, mixtures thereof and the like.

Antimicrobial and antifungal actives can be effective to prevent the proliferation and growth of bacteria and fungi. Nonlimiting examples of antimicrobial and antifungal actives include b-lactam drugs, quinolone drugs, ciprofloxacin, norfloxacin, tetracycline, erythromycin, amikacin, 2,4, 4'-trichloro-2'-hydroxy diphenyl ether, 3,4,4'-Trichlorocarbanilide (triclocarban), phenoxyethanol, 2,4,4'-Trichloro-2'-Hydroxy Diphenyl Ether (triclosan); and mixtures thereof and the like.

Anti-wrinkle, anti-skin atrophy and skin repair actives can be effective in replenishing or rejuvenating the epidermal layer. These actives generally provide these desirable skin care benefits by promoting or maintaining the natural process of desquamation. Nonlimiting examples of antiwrinkle and anti-skin atrophy actives include vitamins, minerals, and skin nutrients such as milk, vitamins A, E, and K; vitamin alkyl esters, including vitamin C alkyl esters; magnesium, calcium, copper, zinc and other metallic components; retinoic acid and its derivatives (e.g., cis and trans); retinal; retinol; retinyl esters such as retinyl acetate, retinyl palmitate, and retinyl propionate; vitamin B 3 compounds (such as niacinamide and nicotinic acid), alpha hydroxy acids, beta hydroxy acids, e.g. salicylic acid and derivatives thereof (such as 5-octanoyl salicylic acid, heptyloxy 4 salicylic acid, and 4-methoxy salicylic acid); mixtures thereof and the like.

Skin barrier repair actives are those skin care actives which can help repair and replenish the natural moisture barrier function of the epidermis. Nonlimiting examples of skin barrier repair actives include lipids such as cholesterol, ceramides, sucrose esters and pseudo-ceramides as described in European Patent Specification No. 556,957; ascorbic acid; biotin; biotin esters; phospholipids, mixtures thereof, and the like.

Non-steroidal Cosmetic Soothing Actives can be effective in preventing or treating inflammation of the skin. The soothing active enhances the skin appearance benefits of the present invention, e.g., such agents contribute to a more uniform and acceptable skin tone or color. Nonlimiting examples of cosmetic soothing agents include the following categories: propionic acid derivatives; acetic acid derivatives; fenamic acid derivatives; mixtures thereof and the like. Many of these cosmetic soothing actives are described in U.S. Pat. No. 4,985,459 to Sunshine et al., issued Jan. 15, 1991, incorporated by reference herein in its entirety.

Artificial tanning actives can help in simulating a natural suntan by increasing melanin in the skin or by producing the appearance of increased melanin in the skin. Nonlimiting examples of artificial tanning agents and accelerators include dihydroxyacetaone; tyrosine; tyrosine esters such as ethyl tyrosinate and glucose tyrosinate; mixtures thereof, and the like.

Skin lightening actives can actually decrease the amount of melanin in the skin or provide such an effect by other mechanisms. Nonlimiting examples of skin lightening actives useful herein include aloe extract, alpha-glyceryl-L-ascorbic acid, aminotyrosine, ammonium lactate, glycolic acid, hydroquinone, 4 hydroxyanisole, mixtures thereof, and the like.

Also useful herein are sunscreen actives. A wide variety of sunscreen agents are described in U.S. Pat. No. 5,087,445, to Haffey et al., issued Feb. 11, 1992; U.S. Pat. No. 5,073, 372, to Turner et al., issued Dec. 17, 1991; U.S. Pat. No. 5,073,371, to Turner et al. issued Dec. 17, 1991; and Segarin, et al., at Chapter VIII, pages 189 et seq., of Cosmetics Science and Technology, all of which are incorporated herein by reference in their entirety. Nonlimiting examples of sunscreens which are useful in the compositions of the present invention are those selected from the group consisting of octyl methoxy cinnamate (Parsol MCX) and butyl methoxy benzoylmethane (Parsol 1789), 2-ethylhexyl p-methoxycinnamate, 2-ethylhexyl N,N-dimethyl-p-aminobenzoate, p-aminobenzoic acid, 2-phenylbenzimidazole-5-sulfonic acid, oxybenzone, mixtures thereof, and the like.

Sebum stimulators can increase the production of sebum by the sebaceous glands. Nonlimiting examples of sebum stimulating actives include bryonolic acid, dehydroetiandrosterone (DHEA), orizanol, mixtures thereof, and the like.

Sebum inhibitors can decrease the production of sebum by the sebaceous glands. Nonlimiting examples of useful sebum inhibiting actives include aluminum hydroxy chloride, corticosteroids, dehydroacetic acid and its salts, dichlorophenyl imidazoldioxolan (available from Elubiol), mixtures thereof, and the like.

Also useful as actives in the present invention are protease inhibitors. Protease inhibitors can be divided into two general classes: the proteinases and the peptidases. Proteinases act on specific interior peptide bonds of proteins and peptidases act on peptide bonds adjacent to a free amino or carboxyl group on the end of a protein and thus cleave the protein from the outside. The protease inhibitors suitable for use in the present invention include, but are not limited to, proteinases such as serine proteases, metalloproteases, cysteine proteases, and aspartyl protease, and peptidases, such as carboxypepidases, dipeptidases and aminopepidases, mixtures thereof and the like.

Other useful active ingredients in the present invention are skin tightening agents. Nonlimiting examples of skin tightening agents which are useful in the compositions of the present invention include monomers which can bind a polymer to the skin such as terpolymers of vinylpyrrolidone, (meth)acrylic acid and a hydrophobic monomer comprised of long chain alkyl (meth)acrylates, mixtures thereof, and the like.

Active ingredients in the present invention may also include anti-itch ingredients. Suitable examples of anti-itch ingredients which are useful in the compositions of the present invention include hydrocortisone, methdilizine and trimeprazine, mixtures thereof, and the like.

Nonlimiting examples of hair growth inhibitors which are useful in the compositions of the present invention include 17 beta estradiol, anti angiogenic steroids, *curcuma* extract, cycloxygenase inhibitors, evening primrose oil, linoleic acid and the like. Suitable 5-alpha reductase inhibitors such as ethynylestradiol and, genistine mixtures thereof, and the like.

Nonlimiting examples of desquamating enzyme enhancers which are useful in the compositions of the present invention include alanine, aspartic acid, N methyl serine, serine, trimethyl glycine, mixtures thereof, and the like.

A nonlimiting example of an anti-glycation agent which is useful in the compositions of the present invention would be Amadorine (available from Barnet Products Distributor), and the like.

Batting Materials:

The inventive cleansing article includes a layer composed of a batting material having a length (i.e. the major axis) and width (i.e. the minor axis) oriented in the x-y plane and a height oriented along its z axis. The inventive batting material is defined as a continuous fiber network or fibrous assembly containing a large number of fiber to fiber bonds. Such continuous networks of bonded fibers are achieved by using one or a combination of chemically or thermally bonding fibers prior to impregnation with the foamable composition. The batting layer may advantageously have from about 0.25 to about 7 or more fiber to fiber bonds per cubic millimeter. Preferably, the batting layer has about 0.5 to 5 fiber to fiber bonds per cubic millimeter. Most preferably the batting layer has a minimum of about 1 to 3 fiber to fiber bonds per cubic millimeter. Such fiber bonds may be quantified using art recognized or equivalent techniques such as the method described below.

Fibrous structures/assembly described herein are comprised of synthetic and/or natural fibers converted via conventional, well-known nonwoven, woven or knit processing systems or combinations thereof into continuous fibrous structures/assemblies. Generally well known nonwoven processing systems transform fibers and filaments directly into useful cohesive structures with adequate strength that are not manufactured via knitting or weaving. Useful synthetic fibers include but are not limited to polyethylene, polypropylene, polyester, low-melt polyester, viscose rayon, polylactic acid and polyamide and blends/combinations thereof and the like. Further examples of synthetic materials useful as components in the present invention include those selected from acetate fibers, acrylic fibers, cellulose ester fibers, and modacrylic fibers. Examples of some of these synthetic materials include acrylics such as Acrilan®, Creslan®, and the acrylonitrile-based fiber, Orion®; cellulose ester fibers such as cellulose acetate, Arnel®, and Acele®; polyamides such as Nylons (e.g., Nylon 6, Nylon 66, Nylon 610 and the like); polyesters such as Fortrel®, Kodel®, and the polyethylene terephthalate fibers, Dacron®.

Additionally synthetic fibers used herein can be described as staple and continuous filaments including any blend thereof. Non-limiting examples of natural materials useful in the fibrous assembly in the present invention are silk fibers, keratin fibers and cellulosic fibers. Non-limiting examples of keratin fibers include those selected from wool fibers, camel hair fibers, and the like. Non-limiting examples of cellulosic fibers include those selected from wood pulp fibers, cotton fibers, hemp fibers, jute fibers, flax fibers, and mixtures thereof. Additionally fibers used herein may include multicomponent fibers or combinations thereof. Useful fiber deniers included herein range from about 1 denier to 20 denier including any combinations within this range.

With respect to manufacturing methods for nonwovens useful in the present invention, fibers are separated, oriented and deposited on a forming or conveying surface. Methods used to arrange or manipulate fibers described herein into a fibrous assembly include but are not limited to carding/garnetting, airlay, wetlay, spunbond, meltblown, vertical lapping or any combination/iteration thereof and the like. Cohesion, strength and stability may be imparted into the fibrous assembly via a bonding mechanism that include but are not limited to needlepunching, stitch bonding, hydroentangling, chemical bonding and thermal bonding and any combination/iteration thereof and the like. Fibers that comprise a fibrous structure/assembly may also be used that are not chemically, and thermally bonded to one another to supplement the continuous bonded network of the inventive bar. Such structures that form a plurality of fiber to fiber contacts are all well suited for the present invention.

Fibrous Assembly Properties

Fibrous assemblies useful for the present invention can range in basis weight from about 25 g/sq. m to 1000 g/sq. m.

In particular, for suitable lather generation of the inventive cleansing article, fibrous assembly density and therefor porosity (P) are important. Porosity can be defined as the volume fraction of air to fibers within a given fibrous assembly. Porosity can be expressed using following equation:

$$P = \frac{\rho_f - \rho_w}{\rho_f},$$

Where $\rho_f$ is fiber density (g/cm$^3$) and $\rho_w$ is nonwoven density (g/cm$^3$). Note that the fibrous assembly density is based on the apparent thickness of the fibrous assembly structure. Preferably, the fibrous assembly of the present invention should display porosity in the range of from about 0.95 to 0.9999.

Another important material property is the resiliency of the fibrous assembly used in the present invention. Specifically, Percent Energy Loss is an important parameter as it describes the resilience of the substrates to an applied load. % Energy Loss is calculated as follows:

$$\% \ EnergyLoss = \left[\frac{J_T - J_R}{J_T}\right] * 100,$$

Where $J_T$, is the Total Energy required to compress the fibrous assembly with a 100 gram load and $J_R$ is the Recovered Energy during one compression cycle (see Energy Loss Test Method described below). Lower energy loss is seen to correspond to a more resilient fibrous assembly. Preferably, fibrous assemblies of the current invention have percent energy loss values ranging from about 5% to 50%.

Another important property of the batting layer is air permeability. Air permeability preferably is in the range of about 200 to 900 cubic ft/sq. ft/min, more preferably of about 300-700 cubic ft/sq. ft/min. Air permeability may be measured using the methodology described below Some preferred embodiments of useful batting layers include vertical lapped nonwovens, which can be further described as having a given number of pleats per inch. In this regards, pleats per inch is defined as the number of folds present in a one inch of nonwoven. A nonlimiting example of a pleat is illustrated in FIG. 1B as pleat 140. This can be measured by placing two marks one inch apart in the machine direction of the nonwoven. Subsequently, a count the number of folds between the two marks is taken. The resultant count is taken as the pleats per inch. A suitable high bulk corrugated nonwoven fabrics are described in U.S. Pat. No. 3,668,054 to Stumpf issued on Jun. 6, 1972; and U.S. Pat. No. 4,576,853 to Vaughn et al. Issued on Mar. 18, 1986; which are incorporated in their entirety by reference herein.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated. Physical test methods are described below:

EXAMPLE 1

Five cleansing articles according to the invention were fabricated having the foamable compositions given in Tables 1 to 5 using processing methods described below. Weight percentages of each component are provided on an active component basis.

TABLE 1

High Oil Bar A

| Component | Wt % |
|---|---|
| Stearic Acid | 13.09 |
| Propylene Glycol | 4 |
| Glycerin | 4 |
| Sodium Hydroxide | 1.3 |
| Sodium Laureth Sulfate 2EO (70%) | 4 |
| Hydrogenated Cotton Seed Oil | 4 |
| Petrolatum | 1 |
| 12-hydroxy Stearic Acid | 9 |
| Sodium C14-16 Olefin Sulfonate | 3 |
| Cocoamidopropyl Betaine | 6 |
| Titanium Dioxide | 0.75 |
| Sodium Isethionate | 17.89 |
| Sodium Cocoate | 14.88 |
| Zinc Oxide | 0.05 |
| Sunflower Seed Oil | 16 |
| Fragrance | 1 |
| Diphosphoric Acid | 0.02 |
| Tetrasodium EDTA | 0.02 |
| Total | 100 |

TABLE 2

Low-Oil Fibrous Bar

| Component | Wt % |
|---|---|
| Stearic Acid | 11.36 |
| Propylene Glycol | 2.47 |
| Glycerin | 4.00 |
| Sodium Hydroxide | 3.94 |
| Sodium Laureth Sulfate 2EO (70%) | 4.57 |
| Hydrogenated Cotton Seed Oil | 3.95 |
| Petrolatum | 1.00 |
| 12-hydroxy Stearic Acid | 8.00 |
| Sodium C14-16 Olefin Sulfonate | 3.89 |
| Cocoamidopropyl Betaine | 6.00 |
| Sodium Tallowate | 6.34 |
| Sodium Isethionate | 11.98 |
| Sodium Cocoate | 11.35 |
| Zinc Oxide | 0.03 |
| Sunflower Seed Oil | 6.00 |
| Disodium Cocoamphodipropionate | 5.78 |
| Sodium Chloride | 0.03 |
| Deionized Water | 2.27 |
| Sodium Lauryl Sulfate | 6.00 |
| Fragrance | 1.00 |
| Diphosphoric Acid | 0.02 |
| Tetrasodium EDTA | 0.02 |
| Total | 100 |

TABLE 3

Pliable Bar

| Component | % |
|---|---|
| Deionized Water | 66.89 |
| Polyquaternium-10 | 0.1 |
| Sodium Chloride | 0.325 |
| Sodium Hydroxide 50% | 0.048 |
| Glycerin USP | 1.00 |
| Ammonium Lauryl Sulfate | 5.08 |

TABLE 3-continued

Pliable Bar

| Component | % |
|---|---|
| Ammonium Laureth Sulfate 2EO (70%) | 3.97 |
| Cocamide MEA | 0.869 |
| PEG-5 Cocamide MEA | 0.4345 |
| Citric Acid | 0.078 |
| DMDM Hydantoin | 0.017 |
| Cocamidopropyl Betaine | 10.00 |
| Propylene Glycol USP | 0.283 |
| Gelatin | 10.00 |
| Tetrasodium EDTA 39% | 0.05 |
| Dequest 2010 (EHDP) | 0.033 |
| Kathon CG | 0.02 |
| Fragrance | 0.8 |
| Color | 0.0025 |
| Total | 100 |

TABLE 4

High Oil Bar B

| Component | % |
|---|---|
| Stearic Acid | 11.47 |
| 12-Hydroxy Stearic Acid | 9.00 |
| Glycerin USP | 4.00 |
| Propylene Glycol | 4.00 |
| Sodium Hydroxide (50%) | 3.78 |
| Sodium Laureth Sulfate 2EO (70%) | 4.00 |
| Hydrogenated Cotton Seed Oil | 4.00 |
| Sunflower Seed Oil | 11.00 |
| Petrolatum | 1.00 |
| Sodium Cocoate | 12.25 |
| Sodium Tallowate | 5.33 |
| Sodium Lauryl Sulfate | 5.50 |
| Sodium C14-16 Olefin Sulfate | 3.00 |
| Cocoamidopropyl betaine | 6.00 |
| Sodium Isethionate | 11.98 |
| Sodium Chloride | 0.056 |
| Deionized Water | 2.287 |
| Tetrasodium EDTA 39% | 0.044 |
| diphosphoric acid | 0.02 |
| titanium dioxide | 0.25 |
| Zinc Oxide | 0.033 |
| Fragrance | 1.00 |
| Total | 100 |

TABLE 5

High Oil Bar C

| Component | % |
|---|---|
| Stearic Acid | 11.2 |
| 12-Hydroxy Stearic Acid | 6.00 |
| Glycerin USP | 4.00 |
| Propylene Glycol | 4.00 |
| Sodium Hydroxide (50%) | 1.30 |
| Sodium Laureth Sulfate 2EO (70%) | 3.93 |
| Hydrogenated Cotton Seed Oil | 3.00 |
| Sunflower Seed Oil | 20.00 |
| Petrolatum | 1.00 |
| Mineral Oil 1000SUS | 3.00 |
| Lauramidopropyl Betaine | 6.00 |
| Sodium C14-16 Olefin Sulfate | 3.00 |
| Tetrasodium EDTA 39% | 0.02 |
| diphosphoric acid | 0.02 |
| titanium dioxide | 0.75 |
| Fragrance | 1.00 |
| Sodium Isethionate | 17.31 |
| Sodium Cocoate | 14.42 |
| Zinc Oxide | 0.05 |
| Total | 100 |

Preparation Method:

For the compositions listed in Tables 1-5, loading levels of the respective cleansing phase listed above were used to impregnate the batting layer as described below. SF-3 nonwoven material was employed as the batting layer. The bars of tables 1 to 5 are manufactured via melt casting. The components of the foamable compositions are mixed and melted at 100° C. except that the components of the pliable bar are mixed and melted at 65° C. The batting layer is cut to appropriate shape and placed within a suitable mold. The batting layer weight may range from 0.9 to 1.45 grams depending on the basis weight of the batting layer.

Approximately 100-grams of each cleansing component blend is then poured onto the fibrous assembly while in the molten state at temperatures ranging from 60° C. to 100° C. except that the pliable bar composition is poured into the fibrous assembly in molten form at temperatures ranging from 45° C. to 65° C. The cleansing component is poured at temperatures lower than the melting/degradation temperature of the polymer/fiber combination of the batting layer so as not to substantially deform or degrade the fibrous assembly. The resulting intimately blended cleansing component and fibrous assembly is cooled to 21° C. at approx. 50% RH until solidified and the solidified bar is removed from the mold.

Formula: High Oil Bar A (TABLE 1)
Fibrous Assembly: SF-3(X-87) obtained from Structured Fibers Inc., Saltillo, MS

| Denier | % |
|---|---|
| 4 | 25 |
| 6 | 75 |
| Fiber Type | 100% PET |
| Basis Weight (oz/sq. yd) | 5 |
| No of Fiber to fiber bonds/cubic mm | 2.19 |
| % Vol. of Nonwoven to Detergent Phase | 0.306 |
| Total amount of Nonwoven per Article | 1.0 grams |
| Total Amount of Detergent Phase | 100.0 grams |
| Ratio of Detergent Phase by Wt of Fibrous Assembly | 100 to 1 |

Formula: Low Oil Fibrous Bar (TABLE 2)
Fibrous Assembly: SF-3(X-87) obtained from Structured Fibers Inc., Saltillo, MS

| Denier | % |
|---|---|
| 4 | 25 |
| 6 | 75 |
| Fiber Type | 100% PET |
| Basis Weight (oz/sq. yd) | 5 |
| No of Fiber to fiber bonds/cubic mm | 2.19 |
| % Vol. of Nonwoven to Detergent Phase | 0.306 |

-continued

| Formula: Low Oil Fibrous Bar (TABLE 2) Fibrous Assembly: SF-3(X-87) obtained from Structured Fibers Inc., Saltillo, MS | |
|---|---|
| Denier | % |
| Total amount of Nonwoven per Article | 1.0 grams |
| Total Amount of Detergent Phase | 114.0 grams |
| Ratio of Detergent Phase by Wt of Fibrous Assembly | 114 to 1 |

| Formulas: Pliable Bar, High Oil Bars B & C (TABLES 3-5) Fibrous Assembly: SF-3(X-87) obtained from Structured Fibers Inc., Saltillo, MS | |
|---|---|
| Denier | % |
| 4 | 25 |
| 6 | 75 |
| Fiber Type | 100% PET |
| Basis Weight (oz/sq. yd) | 5 |
| No of fiber to fiber bonds/cubic mm | 2.19 |
| % Vol. of Nonwoven to Detergent Phase | 0.509 |
| Total amount of Nonwoven per Article | 1.25 grams |
| Total Amount of Detergent Phase | 114.0 grams |
| Ratio of Detergent Phase by Wt of Fibrous Assembly | 91.2 to 1 |

Percent Volume is calculated by using the following relation;

$$\% \, Vol = \frac{Vol_{NW}}{Vol_D} * 100,$$

Where $Vol_{NW}$ is the volume of the nonwoven used in 1 cleansing article and $Vol_D$ is the volume of detergent phase used in 1 cleansing article. The volume of the nonwoven is achieved by dividing the nonwoven density by the total wt. of nonwoven used on one cleansing article.

EXAMPLE 2

The Detergent Phase Yield Stress of the bars prepared in Example 1 was measured according to the procedure described below and the results are summarized in Table 6.

TABLE 6

| Formula | Fibrous Assembly | Yield Stress* |
|---|---|---|
| Low Oil Fibrous Bar | SF-3 | 311.71 |
| Pliable Bar | SF-3 | 216.85 |

*Note: diameter of wire used in yield stress measurement is 0.336 mm

EXAMPLE 3

The Lather improvement factor (LFI) of the bars prepared in Example 1, with (i.e. inventive) and without (i.e. comparative) the batting layer was measured according to the procedure described below and the results are summarized in Table 7 which displays the lather volume measured for each case. The presence of the batting layer increased lather generation by a factor of 1.47 to 2.0 for all the inventive examples studied.

TABLE 7

Lather Volume and Lather Volume Improvement (LFI) factor of Toilet Bar with (inventive) and without (comparative) SF-3 batting layer

| Toilet Bar | Comparative case (ml) | Inventive case (ml) | LFI |
|---|---|---|---|
| Low Oil Fibrous Bar | 115 | 201.67 | 1.75 |
| High Oil Fibrous Bar A | 90 | 188.33 | 2.09 |
| Pliable Bar | 160 | 236.67 | 1.47 |

EXAMPLE 4

The Lather Improvement Factor and Lather Volume of various comparative toilet bars described in Tables 8 to 12 below containing various substrates were compared to the inventive bars of Example 1 using the test methods described below. Methods of preparation of the comparative toilet bars used for the comparison are also provided below.

TABLE 8

Description:

A seamless pad comparative article was prepared from a needlepunched nonwoven described in Table 8b. The cleansing phase composition was prepared from a tallow/coco soap according to the composition listed in Table 8a.

TABLE 8a

| Formula | % by wt. |
|---|---|
| Hydroxyethane Diphosphonic Acid | 0.038 |
| Phosphoric Acid 75% | 0.192 |
| Sodim Tallowate | 61.07 |
| Sodium Cocoate | 13.4 |
| Sodium Hydroxide 50% | 23.46 |
| Sodium Chloride | 0.21 |
| Tetrasodium EDTA 39% | 0.0732 |
| Fragrance Zeta 75 | 1.44 |
| Green Aloe Dye Premix - Bars | 0.09 |

TABLE 8b

Fibrous Structure - Needlepunched 100% PET

| Property | Value |
|---|---|
| Basis weight: | 160 g/m² |
| Thickness: | 5 mm |
| Weight of Nonwoven: | 4.0 grams |
| Weight of Soap: | 80.0 grams |
| Soap to Nonwoven Wt. Ratio: | 20:1 |

TABLE 9

Description:

A comparative cleansing article was prepared using the tallow/coco soap composition of Table 8a. This composition was impregnated into nonwoven synthetic fibers arranged in a lofty three-dimensional random arrangement and bonded together to form a plurality of interconnecting voids, i.e. HDK style # 401 (obtained from HDK Industries, Rogersville, TN) with a basis weight of 160 g/m² and a thickness of 5-mm (see table 9b).

TABLE 9b

Fibrous Structure - Nonwoven 100% PET HDK Style # 401

| Property | Value |
| --- | --- |
| Basis weight: | 160 g/m$^2$ |
| Thickness: | 5 mm |
| Weight of Nonwoven: | 4.0 grams |
| Weight of Soap: | 80.0 grams |
| Soap to Nonwoven Wt. Ratio: | 20:1 |

TABLE 10

Description:

A comparative cleansing article was prepared using a foamable composition composed of vegetable oil and glycerin and an imbedded scrubber of a scrim mesh material. The soap component was selected to be a Moisturizing Clear Glycerin Soap (Life of the Party ™) from Michaels ®, located in Milford, CT. The embedded Scrubber was Nylon Scrim netting from Conwed Inc. located in Minneapolis, MN, Style No. ON3990, 15 g/m$^2$, ¼ in mesh size. The following manufacturing method was used: 100 grams of Moisturizing Clear Glycerin Soap (Life of the Party ™) was melted and poured into PVC plastic soap mold. A 3" × 8" sample of CONWED style ON3990 nylon scrim netting was added to molten soap such that scrim is partially exposed.
The mold was kept at 40 C. for 2 hours to cool.

TABLE 11

Description:

A comparative cleansing article was prepared using a foamable composition composed of the soap component described in Table 9a and an imbedded scrubber of a scrim mesh material (Conwed Inc style ON3990). The following manufacturing method was used:
100 grams of the formula was melted at 100° C. Approximately 50 grams of the foamable composition was placed in mold. A 1" × 1" sample of the nylon scrim netting was added to in the soap bar center. Another 50 grams was placed in mold onto scrim netting.
The mold was kept at 40 C. for 2 hours to cool and solidify.

TABLE 12

Description:

A comparative cleansing article was prepared using a foamable composition composed of the soap component Moisturizing Clear Glycerin Soap (Life of the Party ™), and the fibrous elements were selected to be noncontinous discrete 6 den PET Fibers, 1.5 inches in length (Style # 295 supplied by KOSA Inc. (Spartanburg, SC). The manufacturing process used was as follows:
0.6 grams of 6 den PET was placed in empty PVC plastic soap mold. 80 grams of Moisturizing Clear Glycerin Soap (Life of the Party ™) was melted and poured over fibers in PVC plastic soap mold. The mold placed in 40 C. for 2 hours to cool until the composition solidified.

Lather Volume Results

Table 13 displays the average lather volume for all samples studied. Note that the inventive High Oil Fibrous Bar A, Low Oil Fibrous Bar and Pliable Bar (tables 1-3 respectively) all produced substantially more lather than all the comparative samples and a comparative commercially available noncontinuous fibrous bar, Johnson and Johnson Scrub Bar®. Factor analysis revealed that differences between all bars was significant at the 95% confidence level (p-value<0.05).

TABLE 13

Lather Volume Comparison: Comparative vs. Inventive Bars

| | Average mls |
| --- | --- |
| Comparative Bars | |
| Table 8 | 70 |
| Table 8 | 70 |
| Table 9 | 70 |
| Table 10 | 24 |
| Table 11 | 90 |
| Table 12 | 47 |
| Johnson & Johnson Scrub Bar ® | 160 |
| Inventive Bars | |
| Table 1: High Oil Fibrous Bar A | 188.33 |
| Table 2: Low Oil Fibrous Bar | 201.67 |
| Table 3: Pliable Bar | 236.67 |

EXAMPLE 5

The effect of nonwoven structure parameter porosity (P) on the lather volume and lather improvement factor of article toilet bars having the composition provided in table 1 were also studied for several comparative and inventive cases. Three fibrous structures were used to assess the effect of porosity on lather volume: LPDEN (Supplied by Leggett and Platt Inc., located in Salisbury, N.C.). SF 30-A200-X-87 and SF-3-X-89 (both supplied by Structured Fibers Inc., (Saltillo, Miss.). Large increases in lather volume were observed when a nonwoven is present in a toilet bar and are illustrated in table 14.

TABLE 14

Lather Volume and Lather Improvement Factor ("LIF")

| Nonwoven | With Nonwoven Lather Volume (ml) | Without Nonwoven Lather Volume (ml) | LIF |
| --- | --- | --- | --- |
| LP Den | 195 (comparative) | 150 (comparative) | 1.3 |
| SF 30-A200 | 205 (inventive) | 150 (comparative) | 1.366 |
| SF3 | 225 (inventive) | 150 (comparative) | 1.5 |

Increases in lather volume were found to be associated with increases in the volume fraction of air in a substrate (or porosity). Increased lather volume is a useful property of the present invention.

EXAMPLE 6

The effect of resiliency of the fibrous substrate (e.g. nonwoven) was studied and was found to affect aesthetics when the inventive cleansing article is used to clean the skin. More resilient structures were found to maintain adequate dimensional stability over time and over larger number of uses compared to samples that have comparatively poorer resiliency. Specifically, the Percent Energy Loss was found to be an important parameter as it describes the resilience of the substrates to an applied load (see test method below). Lower energy loss corresponded to a more resilient fibrous substrate with better in-use properties.

Table 15 displays the energy loss and porosity for various inventive and comparative fibrous or nonwoven batting layer samples prior to being impregnated with a foamable composition. Note that samples SF 1, SF 30 A200 and SF3 display the lowest % energy loss values and hence are more resilient than the other samples tested. Inventive toilet bars manufactured with low energy loss nonwovens have high consumer appeal due to improved in-use aesthetics using test panel methodology. Consequently comparative fibrous substrates with high-energy loss are disadvantageous (e.g. Sample LPDEN), as they display poor resiliency. High %-energy loss values determined for samples LPDEN, DKCPTC, KC-Baby, LP-1, and CAR3 preclude their use as adequate fibrous structures in terms of in-use functionality.

Inventive samples SF1, SF30 A200 and SF3 produce adequate lather and display improved functionality because of the high porosity values and low %-energy values determined for these samples. Surprisingly it was found that low %-energy loss values have a positive impact on product functionality in-use (i.e. high consumer appeal) when coupled with relatively high porosity values.

TABLE 15

Fibrous Structures Porosity and % Energy Loss

| Sample | | Porosity | % Energy Loss |
|---|---|---|---|
| | Comparative | | |
| 1 | Table 8 | 0.98444 | 35.13 |
| 2 | Table 8 | 0.98444 | 35.13 |
| 3 | Table 9 | 0.98444 | 35.13 |
| 4 | Table 10 | 0.95447 | 41.23 |
| 5 | Table 11 | 0.95447 | 41.23 |
| 6 | Table 12 | NA (1) | NA (1) |
| 7 | J & J Scrub Bar ® | NA (1) | NA (1) |
| 8 | LPDEN | 0.98349 | 39.78 |
| 9 | DKCPTC | 0.99373 | 31.72 |
| 10 | KC-Baby | 0.99399 | 33.79 |
| 11 | LP-1 | 0.99561 | 30.08 |
| 12 | CAR 3 | 0.99705 | 41.85 |
| | Inventive | | |
| 13 | CPT3 | 0.99732 | 24.57 |
| 14 | SF1 | 0.99385 | 9.336 |
| 15 | SF30 A200 | 0.99383 | 13.08 |
| 16 | SF3 | 0.99514 | 15.79 |

Note
(1): Fibrous substrate is not a continuous network.

EXAMPLE 7A

The effect of substituting four commercially available comparative foam or sponge substrates for the inventive fibrous substrate was studied with respect to the production of lather volume of the cleansing article. Four comparative bars with the foam substrates described in Table 16 were made with the cleansing formulation described in the preparation method below. It was found that the lather volume of each of the comparative bars was substantially less than that obtained from the inventive fibrous substrate and the same formulation. The results are summarized in Table 16 below. The lather volume and porosity of the foam substrates were measured according to the methods described below.

TABLE 16

| | Comparative foam layer containing bars. Comparative Bar | | | |
|---|---|---|---|---|
| | Foam Style # (Note) | | | |
| Property measured | 69620553 (Yellow) | 46200 (Green) | 61202 (Grey) | 182 (Red) |
| Wt of Foam in Bar (grams) | 3 | 1.49 | 1 | 0.8 |

TABLE 16-continued

| | Comparative foam layer containing bars. Comparative Bar | | | |
|---|---|---|---|---|
| | Foam Style # (Note) | | | |
| Property measured | 69620553 (Yellow) | 46200 (Green) | 61202 (Grey) | 182 (Red) |
| Wt. Of Soap in Bar (grams) | 100 | 100 | 100 | 100 |
| Porosity of bar with soap | 0.953294 | 0.97687 | 0.980539 | 0.984431 |
| lather Volume (mls) | 100 | 116.67 | 100 | 108.33 |

Note:
Foam supplied by General Foam Corporation (Paramus, NJ)

EXAMPLE 7B

Several replicates of a single selected commercially available comparative foam substrate Foam Style #182 (Red) was studied with respect to lather volume. Replicate comparative bars with the substrate were made with the formulation described in the preparation method below. It was found that the lather volume of each of the replicate comparative bars was substantially less than that obtained from the inventive fibrous substrate and the same formulation. The lather volume and porosity of the foam substrates were measured according to the methods described below and are summarized in Tables 17 & 18 below.

TABLE 17

| Replicate | Lather Volume |
|---|---|
| 1 | 125 |
| 2 | 100 |
| 3 | 75 |
| 4 | 125 |
| 5 | 100 |
| 6 | 100 |
| 7 | 150 |
| 8 | 100 |
| 9 | 100 |
| 10 | 100 |
| 11 | 100 |
| 12 | 100 |
| Average | 106.25 |

TABLE 18

| Replicate | Porosity |
|---|---|
| 1 | 0.953294 |
| 2 | 0.976802 |
| 3 | 0.980539 |
| 4 | 0.973533 |
| 5 | 0.984431 |
| Average | 0.97372 |

EXAMPLES 7A & B

Preparation Method

The foaming composition of Table 2 was used to impregnate the comparative foam layer. The bars were manufactured via melt casting. The components of the foamable composition are mixed and melted at 100° C. The foam layer is cut to appropriate shape and placed within a suitable mold. The foam layer weight ranged from 0.8 to 3.0 grams. Approximately 100 grams of the cleansing component blend was poured onto the foam while in the molten state at a temperature in the range of 60° C. to 100° C. but below the melting or degradation temperature of the foam so as not to substantially deform or degrade the foam layer. The resulting intimately blended cleansing component and foam assembly was cooled to 21° C. at approx. 50% RH until solidified and the solidified bar removed from the mold. For example the average values for the ratio of % vol. of foam layer to detergent phase volume was 0.306, total amount of foam layer per article was 1.0 gram, total amount of detergent phase was 100 grams, and weight ratio of detergent phase to the foam layer was 100 to 1.

DESCRIPTION OF TEST METHODS

A. Zein Test Method

The surfactant(s) or cleansing base of the inventive toilet bar preferably have zein solubilities of under about 50, 40, 30, and most preferably under about 25 using the zein solubility method set forth below. The lower the zein score, the milder the product is considered to be. This method involves measuring the solubility of zein (corn protein) in cleansing base solutions as follows:

0.3 g of cleansing base and 29.7 g of water are mixed thoroughly. To this is added 1.5 g of zein, and mixed for 1 hour. The mixture is then centrifuged for 30 minutes at 3000 rpm. After centrifugation, the pellet is extracted, washed with water, and dried in a vacuum oven for 24 hours until substantially all the water has evaporated. The weight of the dried pellet is measured and percent zein solubilized is calculated using the following equation:

% Zein solubilized=100 (1-weight of dried pellet/1.5).

The % Zein is further described in the following references: E. Gotte, Skin compatibility of tensides measured by their capacity for dissolving zein protein, Proc. IV International Congress of Surface Active Substances, Brussels, 1964, pp 83-90.

B. Lather Improvement Factor Test Method

Figure 5:
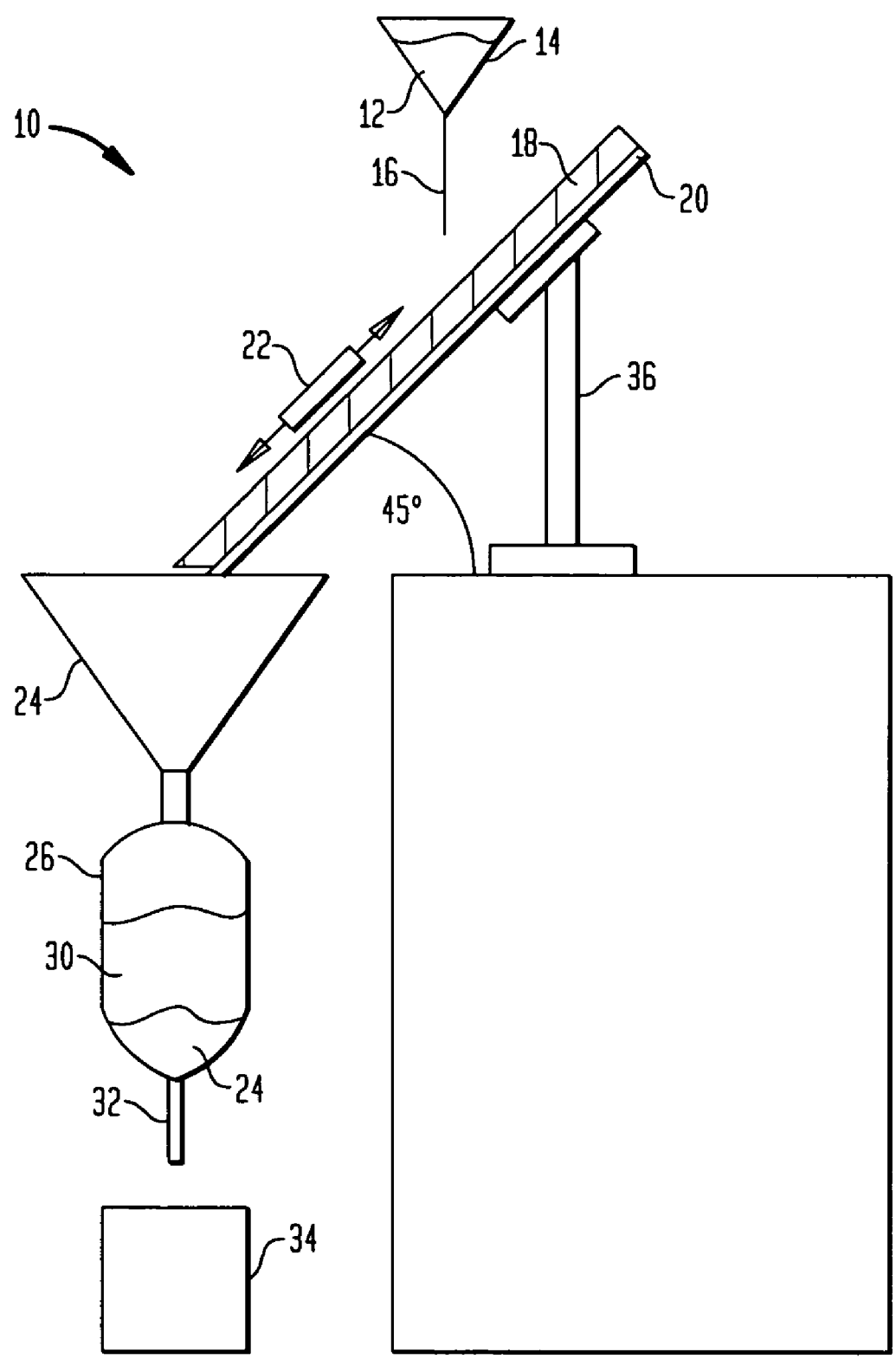
FIG. 5 is a schematic diagram of a suitable apparatus for carrying out the lather volume test method.

This test is used to assess how the addition of fibrous assemblies within toilet bars improves lather generation. A schematic diagram of a suitable test apparatus is illustrated in FIG. 5.

Methodology:

Materials:
Support sheet
Clamping devices
Funnels
Separatory Funnel marked at 50-ml intervals
Beakers
Pipette with a 4 mm orifice opening.
½" Bubble wrap (e.g. S-3930 distributed by Uline Inc. Newark, N.J.

Method:

Referring to FIG. 5 using the lather generation apparatus (10), repeat the following procedure for a bar with the fibrous substrate and a bar without the fibrous substrate.

1 Pour 200 ml of 38° C.±2° C. water (12) contained in funnel (14) at a rate of 5.26 ml/sec through pipette (16) on to the upper edge of bubble wrap (18) fixed in position and supported on sheet (20) and inclined at an angle of 45 degrees from level. Sheet (20) is supported in a fixed position by stand (36).

2 Simultaneously, while pouring water (12) over bubble wrap (18), scrub the wetted bubble wrap (18) with toilet bar (22) in an oscillatory fashion using approximately 15 cm strokes while applying a low level of force pressing the bar to the wrap (approximately ¼ lbs) with sufficient frequency so that 60-70 up and down strokes are completed before the 200 mls of water (12) has passed over bubble wrap (18).

3 Pour an additional 100-ml of 38° C.±5° C. water (12) on to the upper edge of bubble wrap (18) in step 2 to collect Lather (30) in separatory funnel (26) via funnel (24) while stopcock (32) is closed.

4 Slowly rotate stopcock (32) so as to release water (28) from the bottom of separatory funnel (26). When all of the water (28) is removed, close stopcock (32) and read lather (30) volume in mls.

Note: Bubble wrap (18) should be replaced after 10 tests with a new sheet.

For Each Formula Tested, Report:
$L_{WO}$=Lather Volume without substrate (ml)
$L_W$=Lather Volume with Substrate (ml)
LIF=Lather Improvement Factor, Calculated as follows $$LIF = \frac{L_W}{L_{WO}}$$

C. Percent Energy Loss Test Procedure:

Introduction:

Percent Energy Loss describes the resilience of a fibrous substrate to an applied load Materials:

Instron Tensile/Compression Testing Machine (e.g. Instron Model No 4501 with load cell 226.98 N load Cell)
1.5 inch circular die (sample cutting)

Sample Materials

Test Parameters:

| | |
|---|---|
| Compression cycle Strain rate | 38 mm/min |
| Recovery Cycle Strain rate | 38 mm/min |
| Maximum Load: | 100 grams load (~.98 N) |
| Load Cell | 5 N |
| Platen Separation: | 31.75 mm |

Determine:

Total Energy required to compress a sample to 100 grams load.

Recovered Energy from one compression cycle.

% Energy Loss, calculated as follows $$\% \, EnergyLoss = \left[\frac{J_T - J_R}{J_T}\right] * 100$$

% Energy Loss is the resiliency of substrate i.e. the ability to recover compressive force $J_T$=Total Energy Required to Compress material to 100 grams $J_R$=Recovered Energy during one compression cycle D. Toilet Bar Yield Stress (Cheese Cutter) Method Cleansing article yield stress is a measure of the relative softness of toilet bars with the batting layer present. A wire penetrating into the cleansing article with a constant force will come to rest when the force on the wire due to stress balances the weight applied to the wire. The stress at the equilibrium point is described as yield stress ($\sigma_o$). The method may also be usefully employed on a sample of the foamable composition alone.

Materials:
Toilet bar samples
Cheese Cutter Device
Ruler
Weights (4-6 100-g weights)

Procedure:

Cut a square of cleansing article (1.25"×1.25"×2") and position on yield stress device. Place 400-grams on the device while holding the arm. Lower to the arm such that the wire comes in to contact with sample. Release the arm and let the wire penetrate the article for 1 minute. Push the soap through the wire horizontally to cut a wedge out of the sample. Measure and record the length of cut in the sample. Record the temperature. Use the following equation to calculate the yield stress ($\sigma_o$) in kPa.

$$\sigma_o = \frac{0.375 \, mg}{l \, D},$$

Where,
m=mass of driving wire (mass placed on device plus 56 grams)
g=gravitational constant (9.8 m/s$^2$
l=length of wire penetrating soap after 1 minute (mm)
D=diameter of wire (mm)

E. Air Permeability Methodology

The Air Permeability is related to the amount of lather that can be generated by a particular batting material. The Air Permeability (^) is proportional to the density and amount of lather that a particular batting material is capable of generating. The Air Permeability values of the present invention were determined using ASTM Method—Designation D 737-96.

Testing Components:
1. Test head that provides a circular test area of 38.3 cm 2±0.3%;
2. Clamping system to secure test specimens, of different thickness' under a force of at least 50±5N to the test head without distortion and minimal edge leakage underneath the test specimen;
3. A suitable means to minimize edge leakage (e.g., use a 55 Type A durometer hardness polychloroprene (neoprene) sealing ring 20 mm wide and 3 mm thick) around the test area above and underneath the test specimen;
4. Means for drawing a steady flow of air in a normal direction through the test area and for adjusting the airflow rate that preferably provides pressure differentials of between 100 and 2500 Pa (10 and 250 mm or 0.4 and 10 in. of water) between the two surfaces of the substrate being tested. (At a minimum, the test apparatus must provide a pressure drop of 125 Pa (12.7 mm or 0.5 in. of water) across the specimen.);
5. Pressure gauge or manometer, connected to the test head underneath the test specimen to measure the pressure drop across the test specimen in Pascals (mm or in.) of water with an accuracy of ±2%;
6. Flowmeter, volumetric counter or measuring aperture to measure air velocity through the test area in cm 3/s/cm 2 (ft 3/min/ft 2) with an accuracy of ±2%;
7. Calibration plate, or other means, with a known air permeability at the prescribed test pressure differential to verify the apparatus is functioning properly;
8. Means of calculating and displaying the required results, e.g., scales, digital display, and computer-driven systems; and
9. Cutting dies or templates, to cut substrate specimens having dimensions at least equal to the area of the clamping surfaces of the test apparatus.

The substrate samples are cut to the appropriate size (size of clamping surface) using a cutting die. The samples are then preconditioned by bringing them to approximate moisture equilibrium in the standard atmosphere for preconditioning textiles i.e. 21 C AND 65 RH.

Once the samples are preconditioned, bring the samples to moisture equilibrium for testing in the standard atmosphere for testing textiles which is 21° C.±1° C. and 65±2% relative humidity. Handle the test samples carefully to avoid altering the natural state of the samples. Place each test sample in the test head of the test apparatus, and perform the test as specified in the manufacturer's operating instructions. Run test using a water pressure differential of 125 Pa (12.7 m or 0.5 in. of water). Record the individual test sample results in ft 3/min/ft 2. These results represent the Air Permeabilities of the samples.

F. Fiber to Fiber Bond Determination Methodology

Materials:
1. Microscope
2. Camera with back lighting.
3. Glass Slides.
3. Nonwoven Samples Procedure:
1. Prepare a 4 mm×25 mm×25 mm section of nonwoven sample.
2. Place sample on glass slide and secure with tape (sample slide).
3. Prepare another glass side by placing a 1 mm×1 mm mark on surface (reference slide).
4. Photograph reference slide under microscope at 10× magnification.
5. Measure length of mark on photo in mm. Record for later use.
6. Photograph (×5) sample slide under microscope at 10× magnification.
7. Prepare 3 other sample slides and repeat step 6.
8. Count number of fiber to fiber bonds on each photo. Using scale created from reference slide, calculate the actual area each sample slide represents. Divide the number of fiber to fiber bonds by actual area (mm2). Average all measurements.

Calculating No. of Fiber to Fiber Bonds/mm3

Each image can be expressed as a given volume V, (that is one fiber diameter thick). Assuming perfect fiber packing and no air voids between fibers calculate a the no. of fiber to fiber bonds per cubic millimeter. Given a porosity (P), where porosity is the volume fraction of fiber to air in a given nonwoven sample, calculate the number of contacts per cubic millimeter for a given nonwoven having porosity P.

Image Volume
Volume (V)=image area(mm2)*fiber diameter(mm)
No of Fiber to fiber bonds per mm3 (TC)
TC=CP/V
CP=No. of fiber to fiber bonds taken from sample image
Actual No. of Fiber to fiber bonds (AC)
AC=TC*(1-Porosity)

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

What is claimed is:

1. A cleansing article, comprising:
   a. a fibrous layer composed of a continuous network of bonded fibers, said layer having a porosity of greater than about 0.95 and a percent energy loss of less than about 30;
   b. a solid or semi-solid foamable composition, said layer being partially encompassed by said composition, the foamable composition to the layer being in the weight ratio range of about 30 to 1 to about 2000 to 1;
   c. wherein the layer prior to impregnation with the foamable composition is characterized by a non-woven or woven fibrous network selected from one or a combination of the following:
      1. a corrugated bulky fabric having attached pleats oriented substantially perpendicularly to the x-y plane of the cleansing article,
      2. a bulky fabric having a plurality of discrete peaks forming a 3 dimensional pattern where the z axis of the fabric is oriented substantially perpendicularly to the x-y plane of the cleansing article,
      3. a bulky fabric having a polygonal regular or irregular 3 dimensional honeycomb-like structure where the z axis of the honeycomb-like fabric is oriented substantially perpendicularly to the x-y plane of the cleansing article, or
      4. a bulky fabric having a plurality of attached layers oriented substantially perpendicularly to the x-y plane of the cleansing article and arranged in a pattern composed of one or more of spiral, wavy or folded arrangement(s);
   d. wherein the layer prior to impregnation with the foamable composition is characterized by fibers selected from polyethylene terephthalate, polyethylene, polypropylene, nylon, rayon or cotton fibers or blends thereof; and
   e. wherein said article is a toilet bar.

2. The cleansing article of claim 1 wherein the article has a lather improvement factor greater than about 1.25.

3. The cleansing article of claim 1 further comprising an aesthetic ingredient, a skin conditioning ingredient, a skin active ingredient or a blend thereof.

4. The cleansing article of claim 3 wherein the aesthetic ingredient is selected from fragrances, colorants, pigments, cosmetics, suspended bodies or blends thereof; the skin conditioning ingredient is selected from hydrophobic emollients and hydrophilic emollients or blends thereof, and the skin active material is selected from anti-wrinkle ingredients, skin lightening ingredients, vitamins, antimicrobial ingredients, acne medications, exfoliating agents, astringent ingredients, antioxidant ingredients, enzymes, sunscreen ingredients or blends thereof.

5. The cleansing article of claim 1 wherein the foamable composition further comprises an amphoteric surfactant.

6. The cleansing article of claim 1 wherein the foamable composition further comprises a component in a concentration of about 15 to 80% by wt. selected from C8 to C24 acyl isethionate(s), soap(s), or blends thereof.

7. The cleansing article of claim 3 wherein the skin conditioning ingredient includes a hydrophobic emollient selected from silicone oil(s), gum(s); fat(s), di or triglyceride oil(s), wax(es); hydrophobic plant extract(s), fatty acid(s), fatty ester(s), hydrocarbon(s) or blends thereof.

8. The cleansing article of claim 1 wherein the article has a standard lather volume greater than about 150 ml.

9. The cleansing article of claim 1 wherein the fibrous layer has a basis weight in the range of about 1 oz/sq. yd. to 20 oz/sq. yd.

10. The cleansing article of claim 1 wherein the article has a yield stress in the range of about about 50 kPa to 400 kPa at 25 C.

11. The cleansing article of claim 1 wherein the layer prior to impregnation with the foamable composition is characterized by a density of about 0.0041 g/cubic cm. to about 0.1 g/ cubic cm.

12. The cleansing article of claim 1 wherein the layer prior to impregnation with the foamable composition is characterized by an air permeability in the range of about 200 to 900 cubic ft/sq. ft./min.

* * * * *